(12) United States Patent
Vardi et al.

(10) Patent No.: US 10,993,735 B2
(45) Date of Patent: *May 4, 2021

(54) METHOD AND CATHETER FOR CREATING AN INTERATRIAL APERTURE

(71) Applicant: InterShunt Technologies, Inc., St. Louis, MO (US)

(72) Inventors: Gil M. Vardi, Town and country, MO (US); Chris Minar, New Prague, MN (US)

( * ) Notice: Subject to any disclaimer, the term of this patent is extended or adjusted under 35 U.S.C. 154(b) by 342 days.

This patent is subject to a terminal disclaimer.

(21) Appl. No.: 15/900,127

(22) Filed: Feb. 20, 2018

(65) Prior Publication Data

US 2018/0177516 A1  Jun. 28, 2018

Related U.S. Application Data

(63) Continuation of application No. 15/812,815, filed on Nov. 14, 2017, and a continuation-in-part of (Continued)

(51) Int. Cl.
*A61B 17/3205* (2006.01)
*A61B 17/32* (2006.01)
(Continued)

(52) U.S. Cl.
CPC .. *A61B 17/3205* (2013.01); *A61B 17/320016* (2013.01); *A61B 17/32053* (2013.01); *A61B 17/3478* (2013.01); *A61B 34/73* (2016.02); *A61B 2017/003* (2013.01); *A61B 2017/00026* (2013.01); *A61B 2017/00247* (2013.01); *A61B 2017/00331* (2013.01);
(Continued)

(58) Field of Classification Search
CPC ............ A61B 17/32; A61B 17/320016; A61B 17/3205; A61B 17/32053; A61B 2017/00247; A61B 2017/00252; A61B 2017/003; A61B 2017/00318; A61B 2017/00323; A61B 2017/32004; A61B 2017/320056; A61B 2017/320064
See application file for complete search history.

(56) References Cited

U.S. PATENT DOCUMENTS 4,018,228 A   4/1977   Goosen
5,702,412 A   12/1997  Popov et al.
(Continued)

FOREIGN PATENT DOCUMENTS

WO   WO 02/47561 A1   6/2002

OTHER PUBLICATIONS

Barry A. Borlaug, The sHunt for better breathing in heart failure with preserved ejection fraction, European Journal of Heart Failure, 2014, 709-11, vol. 16.
(Continued)

*Primary Examiner* — Ryan J. Severson
(74) *Attorney, Agent, or Firm* — John M. Berns

(57) ABSTRACT

A catheter device 10 with a cutting structure or means 16 on the distal portion 14 is disclosed, along with a medical procedure for using the device. The catheter 10 is configured in such a way as to create a permanent interatrial aperture in the heart, including creating a permanent interatrial hole and/or removing tissue.

18 Claims, 20 Drawing Sheets

Related U.S. Application Data application No. 15/089,547, filed on Apr. 2, 2016, now abandoned, which is a continuation-in-part of application No. 14/738,802, filed on Jun. 12, 2015, now Pat. No. 9,814,483, which is a continuation of application No. 14/738,802, filed on Jun. 12, 2015, now Pat. No. 9,814,483.

(60) Provisional application No. 62/012,212, filed on Jun. 13, 2014.

(51) Int. Cl.

| | | |
|---|---|---|
| *A61B 17/34* | (2006.01) | |
| *A61B 34/00* | (2016.01) | |
| A61B 17/30 | (2006.01) | |
| A61B 17/00 | (2006.01) | |
| A61B 17/22 | (2006.01) | |
| A61B 90/00 | (2016.01) | |

(52) U.S. Cl.
CPC .............. *A61B 2017/22042* (2013.01); *A61B 2017/22044* (2013.01); *A61B 2017/22047* (2013.01); *A61B 2017/22069* (2013.01); *A61B 2017/306* (2013.01); *A61B 2017/320064* (2013.01); *A61B 2017/3458* (2013.01); *A61B 2090/064* (2016.02); *A61B 2090/065* (2016.02)

(56) References Cited

U.S. PATENT DOCUMENTS

| | | |
|---|---|---|
| 5,893,369 A | 4/1999 | LeMole |
| 5,910,153 A | 6/1999 | Mayenberger |
| 6,022,367 A | 2/2000 | Sherts |
| 6,080,173 A | 6/2000 | Williamson et al. |
| 6,428,555 B1 | 8/2002 | Koster, Jr. |
| 6,468,227 B2 | 10/2002 | Zimmon |
| 6,626,921 B2 | 9/2003 | Blatter et al. |
| 6,695,859 B1 | 2/2004 | Golden et al. |
| 6,743,244 B2 | 6/2004 | Blatter et al. |
| 6,863,677 B2 | 3/2005 | Breznock |
| 6,893,449 B2 | 5/2005 | Vargas et al. |
| 7,056,294 B2 | 6/2006 | Khairkhahan et al. |
| 7,144,405 B2 | 12/2006 | Vargas et al. |
| 7,771,442 B2 | 8/2010 | Shriver |
| 7,799,041 B2 | 9/2010 | Beane et al. |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,157,860 B2 | 4/2012 | McNamara et al. |
| 8,172,896 B2 | 5/2012 | McNamara et al. |
| 8,216,265 B2 | 7/2012 | Haunschild et al. |
| 8,226,670 B2 * | 7/2012 | Beane .................. A61B 17/0218 606/153 |
| 8,235,933 B2 | 8/2012 | Keren et al. |
| 8,252,042 B2 | 8/2012 | McNamara et al. |
| 8,328,751 B2 | 12/2012 | Keren et al. |
| 8,460,372 B2 | 6/2013 | McNamara et al. |
| 8,597,315 B2 | 12/2013 | Snow et al. |
| 8,696,611 B2 | 4/2014 | Nitzan et al. |
| 8,740,962 B2 | 6/2014 | Finch et al. |
| 8,745,845 B2 | 6/2014 | Finch et al. |
| 8,752,258 B2 | 6/2014 | Finch et al. |
| 8,771,302 B2 | 7/2014 | Woolfson et al. |
| 8,771,305 B2 | 7/2014 | Shriver |
| 8,882,697 B2 | 11/2014 | Celermajer et al. |
| 8,951,223 B2 | 2/2015 | McNamara et al. |
| 8,956,377 B2 | 2/2015 | Khalapyan |
| 9,005,155 B2 | 4/2015 | Sugimoto |
| 9,034,034 B2 | 5/2015 | Nitzan et al. |
| 9,205,236 B2 | 12/2015 | McNamara et al. |
| 9,232,997 B2 | 1/2016 | Sugimoto et al. |
| 9,277,995 B2 | 3/2016 | Celermajer et al. |
| 9,358,371 B2 | 6/2016 | McNamara et al. |
| 9,629,715 B2 | 4/2017 | Nitzan et al. |
| 9,642,993 B2 | 5/2017 | McNamara et al. |
| 9,649,480 B2 | 5/2017 | Sugimoto et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,757,107 B2 | 9/2017 | McNamara et al. |
| 9,775,636 B2 | 10/2017 | Fazio et al. |
| 9,814,483 B2 * | 11/2017 | Vardi .................. A61B 17/3205 |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,188,375 B2 | 1/2019 | McNamara et al. |
| 2002/0169377 A1 * | 11/2002 | Khairkhahan ....... A61B 5/0084 600/433 |
| 2006/0009715 A1 | 1/2006 | Khairkhahan et al. |
| 2006/0111733 A1 * | 5/2006 | Shriver .................... A61F 2/06 606/153 |
| 2007/0185513 A1 * | 8/2007 | Woolfson ......... A61B 17/32002 606/108 |
| 2010/0010500 A1 | 1/2010 | Beane |
| 2010/0057192 A1 | 3/2010 | Celermajer |
| 2010/0121258 A1 * | 5/2010 | Shriver .......... A61B 17/320758 604/22 |
| 2010/0298850 A1 * | 11/2010 | Snow .............. A61B 17/32075 606/159 |
| 2011/0071623 A1 | 3/2011 | Finch et al. |
| 2011/0218480 A1 | 9/2011 | Rottenberg et al. |
| 2011/0218481 A1 | 9/2011 | Rottenberg et al. |
| 2011/0270239 A1 | 11/2011 | Werneth |
| 2011/0295183 A1 | 12/2011 | Finch et al. |
| 2012/0259263 A1 * | 10/2012 | Celermajer ........... A61F 2/2475 604/8 |
| 2012/0265296 A1 | 10/2012 | McNamara et al. |
| 2012/0289882 A1 | 11/2012 | McNamara et al. |
| 2012/0290062 A1 | 11/2012 | McNamara et al. |
| 2013/0006281 A1 | 1/2013 | Golden et al. |
| 2013/0178784 A1 | 7/2013 | McNamara et al. |
| 2013/0218261 A1 | 8/2013 | Beane |
| 2013/0267885 A1 | 10/2013 | Celermajer et al. |
| 2013/0281988 A1 | 10/2013 | Magnin et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0277039 A1 | 9/2014 | Liberatore et al. |
| 2014/0277043 A1 | 9/2014 | Jenkins et al. |
| 2014/0277045 A1 * | 9/2014 | Fazio .............. A61B 17/320016 606/170 |
| 2014/0277054 A1 | 9/2014 | McNamara et al. |
| 2015/0359556 A1 * | 12/2015 | Vardi .................. A61B 17/3205 606/170 |
| 2016/0270810 A1 * | 9/2016 | Vardi .................. A61B 17/3205 |
| 2018/0064460 A1 * | 3/2018 | Vardi ............... A61B 17/32053 |
| 2018/0177516 A1 * | 6/2018 | Vardi .................... A61B 34/73 |
| 2019/0029705 A1 * | 1/2019 | Vardi ............. A61B 17/320016 |

OTHER PUBLICATIONS

Michael A. Burke et al., Prognostic Importance of Pathophysiologic Markers in Patients With Heart Failure and Preserved Ejection Fraction, Circulation, Heart Failure, Dec. 23, 2013, 288-299, vol. 7.

Rainer Hoffmann, et al., Functional Effect of New Atrial Septal Defect After Percutaneous Mitral Valve Repair Using the MitraClip Device, Am J Cardiol, 2014: 113:1228-1233.

Lourdes R. Prieto, et al., Atrial Septostomy Using a Butterfly Stent in a Patient With Severe Pulmonary Arterial Hypertension, Catheterization and Cardiovascular Interventions, Sep. 12, 2006, 68:642-647.

Paul M. Seib, et al., Blade and Balloon Atrial Septostomy for Left Heart Decompression in Patients with Severe Ventricular Dysfunction on Extracorporeal Membrane Oxygenation, Catheterization and Cardiovascular Interventions, 1999, 46:179-186.

Lars Sondergaard et al., Transcatheter Treatment of Heart Failure with Preserved or Mildly Reduced Ejection Fraction Using a Novel Interatrial Implant to Lower Left Atrial Pressure, European Journal of Heart Failure, Jun. 24, 2014, 16:796-801.

(56) References Cited

OTHER PUBLICATIONS

Ignacio J. Amat-Santos et al., Left Atrial Decompression Through Unidirectional Left-to-Right Interatrial Shunt for the Treatment of Left Heart Failure: First-In-Man Experience with the new V-Wave Device, EuroIntervention, May 2014.

David Kaye, et al., Effects of an Interatrial Shunt on Rest and Exercise Hemodynaics: Results of a Computer Simulation in Heart Failure, Journal of Cardiac Failure, 2014, 20:3:212-21.

* cited by examiner

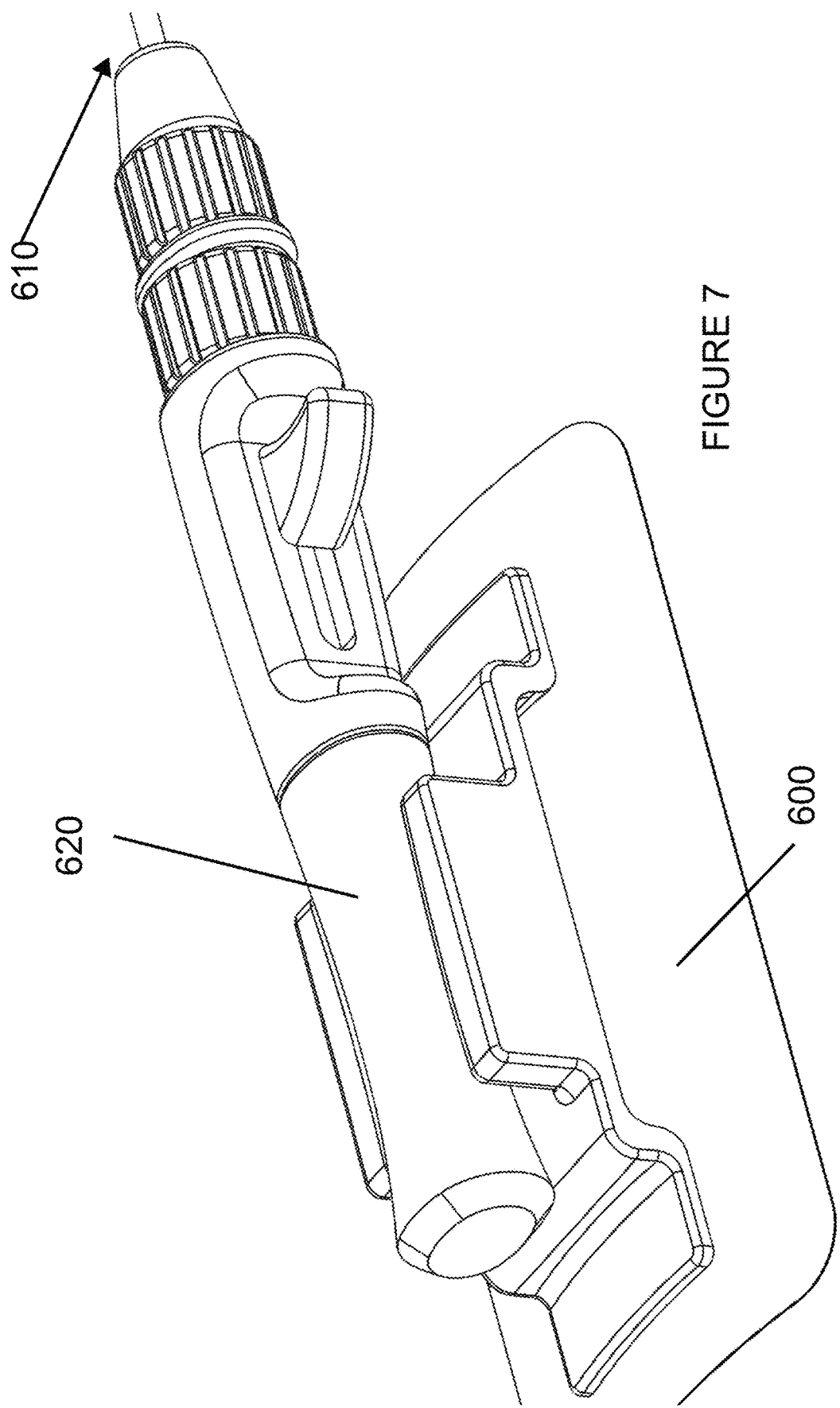

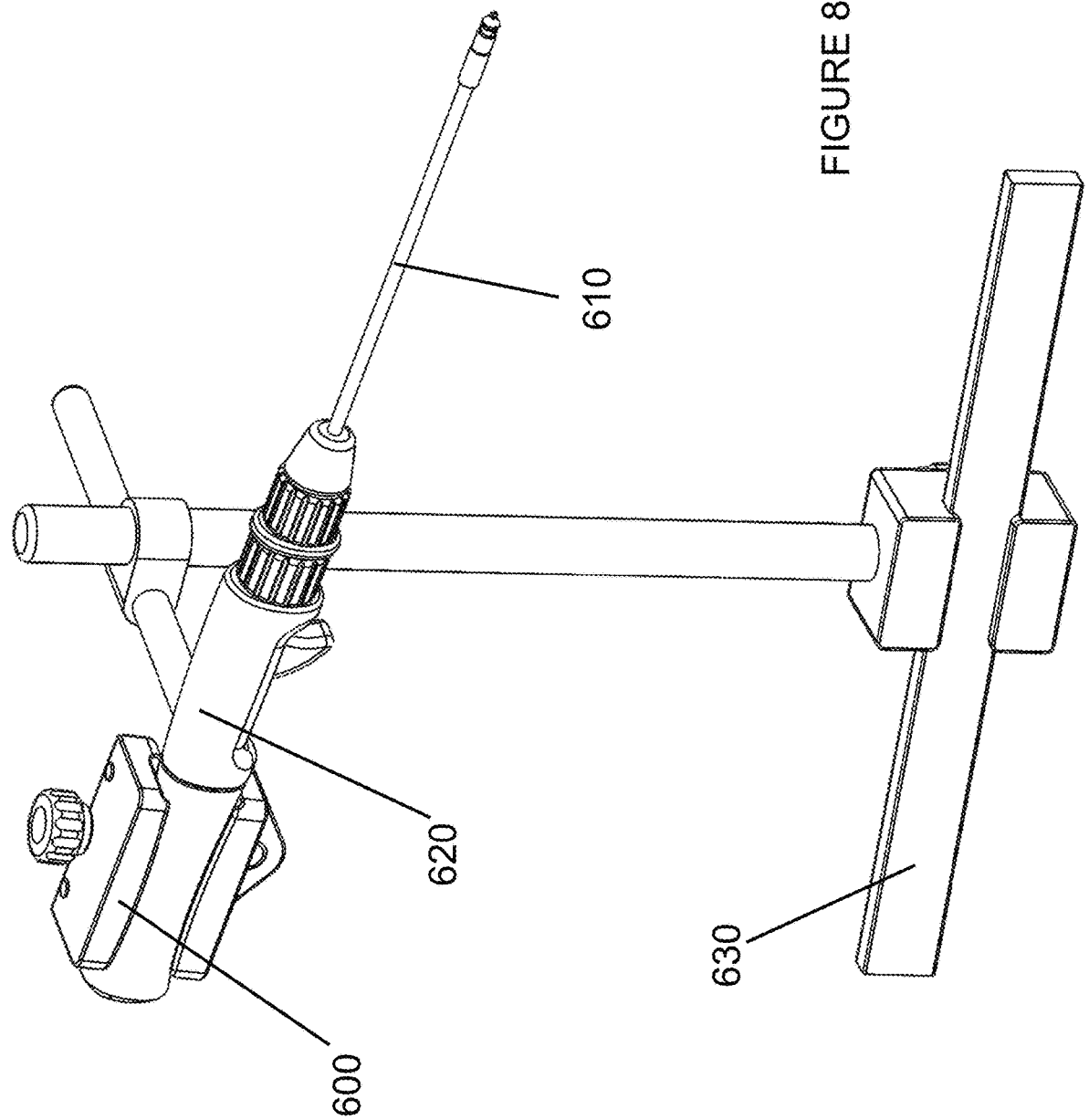

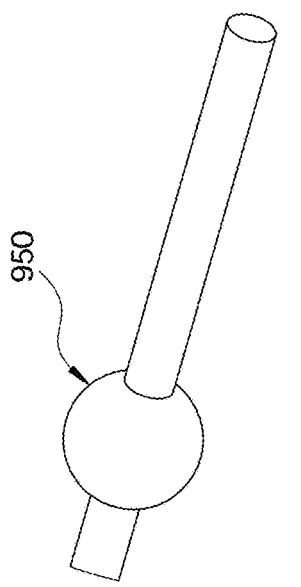
FIGURE 12D
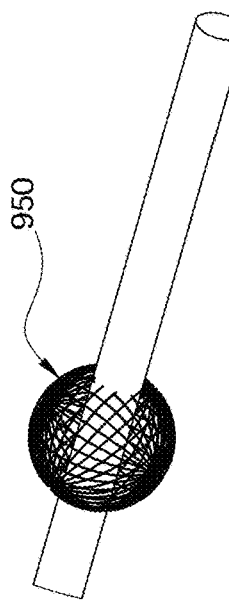
FIGURE 12C
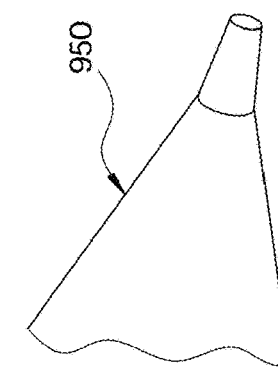
FIGURE 12B
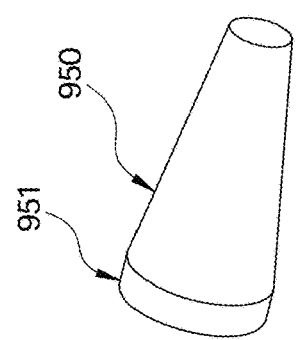
FIGURE 12F
FIGURE 12E
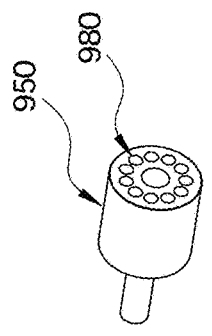
FIGURE 12i
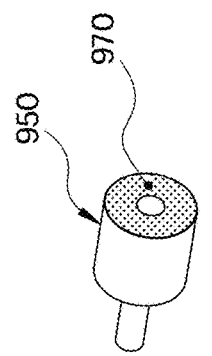
FIGURE 12H
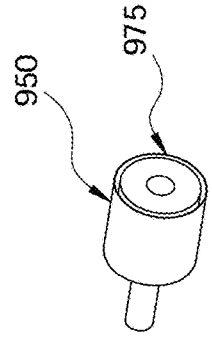
FIGURE 12G

METHOD AND CATHETER FOR CREATING AN INTERATRIAL APERTURE

CROSS REFERENCE TO RELATED APPLICATIONS

This application claims the benefit of priority to U.S. patent application Ser. No. 15/089,547, filed Apr. 2, 2016, U.S. patent application Ser. No. 14/738,802, filed Jun. 12, 2015, now U.S. Pat. No. 9,814,483, which claims priority to U.S. Provisional Application No. 62/012,212 filed Jun. 13, 2014, the entire disclosures of which are hereby incorporated by reference. This application also claims the benefit of priority to U.S. patent application Ser. No. 15/812,815, filed Nov. 14, 2017, which also claims priority to U.S. patent application Ser. No. 14/738,802, filed Jun. 12, 2015, now U.S. Pat. No. 9,814,483, which claims priority to U.S. Provisional Application No. 62/012,212 filed Jun. 13, 2014, the entire disclosures of which are hereby incorporated by reference.

BACKGROUND OF THE INVENTION

Field of the Invention

The invention relates to medical devices and methods of medical treatment. The invention relates to a medical device and method of treatment used to create an aperture in the interatrial septum of a heart.

Background Art

There are some medical conditions that are treated by creating an opening between body chambers in order to create a connection between the chambers. The heart has an interatrial septum or wall that separates the left atrium and the right atrium. In certain heart failure patients (e.g., heart failure with preserved ejection fraction (diastolic dysfunction)) there is a need to allow blood flow from the left atrium to the right atrium to reduce left atrial pressure. Likewise, certain other heart diseases and conditions, such as congenital heart diseases and pulmonary hypertension may be treated by making an interatrial opening; however, the goal is to create a right-to-left shunt to reduce the high right-sided pressure.

One procedure uses a balloon to create a hole in the septum. However, it has been found that a hole created in this manner may not stay open and after a period of time may spontaneously close. This renders this particular therapeutic solution temporary.

A few other devices have been proposed in order to overcome the temporary solution of using a balloon. Implanting a stent in the interatrial septum has been used as a treatment for elevated pressure in one atrium by allowing blood to flow through the opening to the other atrium to reduce atrial pressure. A heart surgeon implants the stents in certain predetermined sizes in an effort to control the amount of blood flow between the atria. Thus, one device is to use a stent to keep the hole open. Another device uses a valve inserted into the septum that keeps the hole open and also assists in controlling blood flow. Significant drawbacks to these devices are that they are permanent implants that can promote thrombosis and are potentially subject to infection.

Another major drawback of these devices is that they are not capable of removing a segment of the septum. The benefit of removing a segment of the septum is that aperture will be less likely to close spontaneously. The stents may also become spontaneously dislodged and embolize and cause cardiac damage or blockage of blood flow.

Therefore, it would be desirable to have a medical device that is capable of creating an incision or an opening in the interatrial septum of the heart to alleviate pressure between chambers in the heart that does not suffer from the limitations of prior devices or procedures. It would be advantageous to have a catheter that can create various slits, openings, or apertures in the interatrial septum in a predetermined orientation. It would also be advantageous to have a catheter that may be easily manipulated to remove a section of the interatrial septum to form a permanent aperture that is less likely to spontaneously close.

BRIEF SUMMARY OF THE INVENTION

The present invention solves these needs by providing a medical device that creates a hole in the interatrial septum and/or removes tissue as needed. In one embodiment a medical device assembly includes a sheath that includes an elongated shaft with a first bend region, a central lumen, a distal end with a distal end lumen and a first steering wire, the steering wire having a first position and a second position, wherein at the first position the first bend region is substantially linear, and wherein at the second position the distal end and the distal end lumen of the sheath are substantially perpendicular to an inter atrial septum. The assembly may also include a catheter inside the sheath, the catheter including a shaft having a central lumen. The assembly also includes a shaped blade that includes a blade cutting edge that is oriented at a substantially right angle to the longitudinal axis of the sheath when the sheath is oriented substantially perpendicular to the inter atrial septum, and is adapted to cut a 3 mm or larger durable aperture in the interatrial septum, a tissue articulator having a first setting and a second setting, the tissue articulator being adapted to hold the interatrial septum against the shaped blade for cutting while in the second setting, and an actuator operably connected to the tissue articulator, the actuator having a first position and a second position, wherein when the actuator is in the second position the tissue articulator holds the interatrial septum against the shaped blade.

In another embodiment, the medical device assembly includes a catheter assembly, the catheter assembly including a catheter shaft, the catheter shaft having a central lumen and a radiopaque marker, a shaped blade with a cutting edge that is oriented at a substantially right angle to the longitudinal axis of the catheter, a proximal tissue retention device, a distal tissue retention device, an actuator configured to reduce a gap between the proximal and distal tissue retention devices and a first steering element configured to orient the shaped blade toward a tissue. The assembly may also have a locking mechanism configured to hold a force on the tissue between the proximal and distal tissue retention devices. In some embodiments the first steering element may be a pull wire, while in others it may be a shape memory material or a preformed bend.

The assembly may also include a sheath that includes a lumen configured to contain the catheter inside the sheath, an elongated sheath shaft, the sheath shaft having a first bend region, a central lumen and a distal end, and where the first steering element is on the sheath, and is configured to move the first bend region from a substantially linear orientation to a second orientation substantially perpendicular to a longitudinal axis of the sheath.

In some embodiments the actuator forces the proximal and distal tissue retention devices together with a preset force. In some embodiments the assembly also includes a second actuator configured to expand the distal tissue retention device. In some embodiments the distal tissue retention device is expandable. The distal tissue retention device may expand to an open position when it exits one of a catheter, a tube, or a sheath.

In some embodiments the proximal tissue retention device and the distal tissue retention device apply a preset force at their outer edge. In some embodiments the outer diameter of the proximal tissue retention device is close fitting to the inner diameter of the shaped blade. In one embodiment the blade has its sharp edge on its inner diameter. The distal tissue retention device may include a tissue trap.

In some embodiments the assembly includes a catheter hub configured to secure the catheter system to a stable object. In some embodiments the assembly includes a marker to identify the catheter location on a visualization system.

In one embodiment the assembly includes a means for rotating the shaped blade. In embodiments the shaped blade comprises an expandable basket with multiple cutting points. The shaped blade may serve as a proximal tissue retention device.

In another embodiment, the invention includes a medical device assembly that includes a catheter assembly with a catheter shaft, the catheter shaft having a central lumen, a shaped blade including a blade cutting edge that is oriented at a substantially right angle to the longitudinal axis of the catheter, a proximal tissue retention device, a distal tissue retention device, an actuator, the actuator configured to force the proximal and distal tissue retention devices together with a preset force, a locking mechanism configured to lock the proximal and distal tissue retention devices in place; and a first steering element configured to re-orient the shaped blade from a first position substantially orthogonal to the longitudinal axis of the catheter to a second position substantially parallel to the longitudinal axis of the catheter.

The invention also includes a method of treating a heart that includes inserting a catheter into the right atrium of the heart, the catheter comprising a shaft, a distal catheter lumen, a shaped cutting blade arranged around the distal catheter lumen, a proximal tissue retention device, the proximal tissue retention device having a first position and a second position, a distal tissue retention device, the distal tissue retention device having a first position and a second position, an actuator connected to at least one of the tissue retention devices, and a steering mechanism. While the catheter is in the right atrium, a portion of the device is moved into the left atrium, and the actuator is actuated to lock the tissue retention devices in place with a portion of the interatrial septum held between them, an aperture is cut in the interatrial septum between the right atrium and the left atrium, and a cut tissue is removed from the right atrium.

BRIEF DESCRIPTION OF THE DRAWINGS

FIG. 7 is a partial perspective view of a catheter hub constructed according to the present disclosure;
FIG. 8 is a partial perspective view of a catheter hub constructed according to the present disclosure;
FIG. 12B is a partial perspective view of the distal end of a catheter constructed according to the present disclosure;
FIG. 12C is a partial perspective view of the distal end of a catheter constructed according to the present disclosure;
FIG. 12D is a partial perspective view of the distal end of a catheter constructed according to the present disclosure;
FIG. 12E is a partial perspective view of the distal end of a catheter constructed according to the present disclosure;
FIG. 12F is a partial perspective view of the distal end of a catheter constructed according to the present disclosure;
FIG. 12G is a partial perspective view of the distal end of a catheter constructed according to the present disclosure;
FIG. 12H is a partial perspective view of the distal end of a catheter constructed according to the present disclosure;
FIG. 12I is a partial perspective view of the distal end of a catheter constructed according to the present disclosure.

DETAILED DESCRIPTION OF THE PREFERRED EMBODIMENTS

Figure 1:
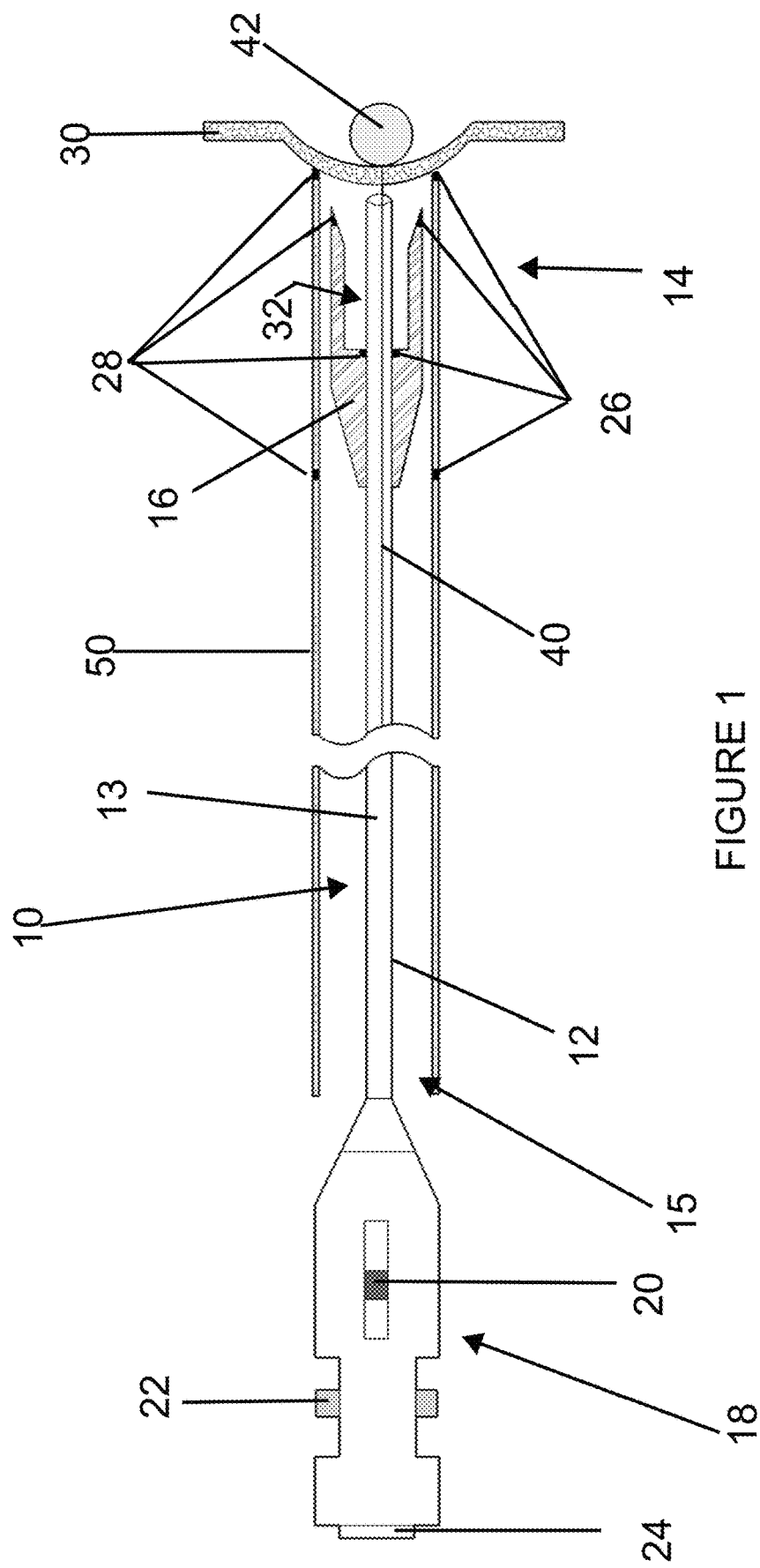
FIG. 1 is a partial perspective view of a catheter constructed according to the present disclosure.

In general, the invention comprises a medical procedure and corresponding medical devices for therapeutic surgical procedures. In particular, the invention comprises a method of creating an aperture between heart chambers for blood flow and devices for creating that aperture. In this context, an aperture creates a space or gap large enough to allow significant blood flow between the two chambers it connects, to treat or improve heart failure, pulmonary hypertension, or similar diseases, without the use of an implanted device.

In order to treat congestive heart failure, it must first be diagnosed. In particular diagnosis may comprise listening to the lungs for signs of congestion, measurement of vital signs, a chest x-ray of the lungs, electrocardiogram (ECG), an echocardiography and other imaging modalities to assess cardiac output, ventricular contraction and filling, atrial size, and cardiac valve function, etc., insertion of a central venous catheter and measurement of pulmonary capillary wedge pressure (PCWP), blood tests, e.g., to check for chemicals such as brain natriuretic peptide (BNP and N-ter final pro-B-type natriuretic peptide (NT-proBNP), a stress test, cardiac catheterization and/or an MRI or CT scan. In addition, transthoracic echocardiography (TTE) or transeophogeal echocardiography (TEE) may be used to confirm the absence of any current holes between the chambers of the heart.

Once congestive heart failure is diagnosed a course of treatment will be designed. While it is possible to treat congestive heart failure with surgery, implants, or other methods, herein disclosed is a method of advantageously treating congestive heart failure without surgery and without leaving behind an implant.

The disclosed procedure preferably begins with a percutaneous entry into a vein, preferably the femoral vein in the groin region. It is also possible to gain entry via a jugular or subclavian vein or neck vein. Typically this introduction is initiated by placing a needle through the patient's skin and into the vein. Then a guidewire is placed thru the needle and run up into the vein. Over this guidewire a combination introducer sheath and dilator is inserted into the vein.

The introducer sheath must have an inside diameter to accommodate the outer diameter of the therapy catheter and system. With the introducer sheath in place in the vein the guidewire is advanced up the IVC and into the right atrium (RA) of the heart. The therapy catheter system may be introduced into the RA as an assembly, or in partial assemblies.

In one partial assembly embodiment the outer catheter torque shaft with cutting blade is mounted to a dilator. This combination is placed through the introducer and advanced into the RA. The tapered dilator tip makes the advancement of the combination easy and safe. Depending on the embodiment, the blade may have a blade protecting cover—discussed in detail below—over it. In another embodiment the blade has the sharp edge on its inner diameter and the inside diameter is close fitting with the outer diameter of the dilator or dilator shaft, and thus the patient is protected from the sharp blade.

After introduction of the cutting blade into the RA the introducer can be retracted, leaving the blade on the torque shaft in the RA. Next the tissue capture components are inserted into the inside of the torque shaft and blade. Alternatively the blade with torque shaft and tissue capture system can be introduced into the RA as a combined assembly with or without the use of a dilator. There are multiple ways of facilitating the latter. First, the cutter shaft can have a movable tapered outer sheath protecting the cutter and capture mechanism, which can be withdrawn once the RA is reached. Alternatively, the distal capture mechanism may have a conical shape to it (tapered balloon, tapered slotted tube, tapered braided tube, etc.) taking the place of the tapered introducer. Finally, the need for a hard taper introducer can be minimized by using an expandable introducer seal (preferably not a hard silicone seal). The sheath used in the present invention may be steerable, for example controlled by pull wires which extend from its distal region to a handle at its proximal end, the handle having one or more actuators. Likewise the sheath may be pre-curved or pre-bent such that it will automatically orient towards the interatrial septum once it reaches the right atrium. The sheath may be magnetically or robotically steerable.

Once in the right atrium, the physician will identify the portion of the interatrial septum at which he will create the interatrial aperture. Typically, this will be at the fossa ovalis. Because the fossa ovalis is thinner than the remainder of the interatrial septum, it will be easiest to cut an aperture at its location. To identify the fossa ovalis the physician may employ one or more means of tissue thickness sensing. For example the physician may use an electrode and test for impedance changes, may employ one or more ultrasound methods, or may simply test for tenting. For example, the physician may apply a small amount of pressure to the interatrial septum and search for tenting in the tissue. Once the physician locates the spot where the tissue easily tents, e.g. the fossa ovalis, the physician will deploy the present device to create the aperture.

Once the entire therapy catheter system is in the RA an expandable distal capture component may be advanced across the atrial septum, preferably close to the center of the fossa ovalis, and into the left atrium (LA). In one embodiment the guidewire the catheter is on may already be across the atrial septum. In other embodiments the distal capture component may cross without a guidewire.

When it is desirable to cross into the left atrium the physician will create a small puncture in the septum using a transseptal device. In some embodiments a guidewire is used to first cross the septum. Guidewire crossing of the atrial septum may be facilitated by a crossing needle like a BRK™ transseptal puncture needle, a Baylis Medical RFG™ transseptal kit, a brockenbrough needle, or another transseptal device may be used for crossing the septum into the left atrium. Alternatively the expandable distal capture component may have a needle type distal tip, an RF electrode on the distal tip, or a similar distal tip to facilitate easy atrial septum crossing without the use of a preplaced guidewire. Once there, the guidewire is threaded through the interatrial septum puncture and the distal end of the guidewire is left in the left atrium. The proximal end of the guidewire will remain outside of the body, with its entry point at the femoral vein. As with the sheath, the guidewires described herein may be pre-curved or pre-bent such that they will automatically orient towards the interatrial septum once reaching the right atrium.

Depending on the therapeutic catheter that will be used in the latter portion of this procedure it is possible that a guidewire may not be required, and in some cases that the device may not cross into the left atrium at all. In such instances a transseptal device may not be necessary either. If the catheter to be used to form the interatrial aperture is designed to create its own transseptal crossing or create an aperture without crossing the septum, the guidewire or transseptal device may be avoided, potentially saving cost and time.

Either way if it is to cross the septum it is helpful for the expandable distal capture component to have certain features, such as one or more of a reduced cross section, expandability, a tapered tip and a lubricious coating. Likewise, to facilitate low force crossing of the septum it is important for the expandable distal capture component to have a low profile. Having a low profile minimizes tissue tearing, which improves accuracy of shunt shape and size. As an example of this, if the distal capture component was not expandable, but instead a tapered shape like a dilator, the tissue will tear or expand when being crossed such that the subsequent capture of tissue can be less than ideal. Portions of the tissue may escape cutting and capture, which can lead to multiple problems. First a tissue portion that has stretched outside or partially outside the range of the cutter may not, then be cut and removed. Over time that stretched or torn tissue may heal, prematurely healing the aperture. Second, such a stretched or torn tissue may come loose, either during the procedure or at a later date, causing a stroke or another complication. This distal capture component must also provide high capture forces when it is expanded, for accurate shunt size and shape. Furthermore, for safety reasons the expandable distal capture mechanism failure mode defaults to open. This means the device is ideally naturally self-expanding after it exits a flexible retention tube. Finally, the capture mechanisms must ideally place most of the capture forces at the outer circumference of the captured area.

A nitinol wire braided or nitinol cut tube formed into a conical shape is one option. The device may ideally be preshaped such that when it comes out of the restraining device it expands, or it may expand to its full shape when the two ends of the device are pulled together. An expandable distal capture mechanism may also be made from an expanded nitinol wire or tube form and held about the catheter axis using radial arms, balloons or similar. Alternatively, high pressure shaped polymer balloons may also be used on their own or in combination with metal expandable structures to make an expandable distal capture component.

With the guidewire in place, the sheath may be removed. If so, a therapy catheter and/or a sheath will be or will have been provided and directed into the right atrium. Once there the therapy catheter, further to the mechanisms disclosed in detail below, will create a durable interatrial aperture.

During the procedure the physician will monitor the location of the catheter and/or sheath as well as the progress of the cut, the nature of the aperture, or other procedure details via fluoroscopy, MRI, ultrasound, or transesophageal echocardiography, intracardiac echocardiography (ICE) or similar tracking or visualization technology for guidance. Toward this end, it is preferred that the catheter includes visualization markers, such as radiopaque or ultrasound markers as described in further detail below. Likewise, the physician may monitor the location of the catheter and/or sheath as well as the progress of the cut, the nature of the aperture, or other procedure details via a camera, such as a CCD camera. In the latter case it may be advantageous to apply a hood over the operation region, empty the hood of blood and replace it with saline, such that the procedure may be visually monitored. This hood may also be used, as discussed in detail in the incorporated priority documents, to provide an orthogonal orientation to the cutting blade and the target tissue. Other location systems are possible, including MRI, electroanatomical navigation systems such as EnSite®, Carto®, or MediGuide® systems, along with the corresponding sensors on the introducer 50 and catheter 10.

The interatrial aperture will be created by one of two mechanisms or a combination thereof. First the surgical catheter will create an aperture. The catheter could use a cutting blade or other means disclosed herein to create an aperture or cut pattern in the interatrial septum such that a sufficient flow of blood may occur between the two atria. For example, the catheter may cut an X-pattern aperture in the septum. Doing so leaves flaps that will open and close depending on the pressure differential between the two atria. Likewise the catheter may create a circular or semi-circular hole in the septum. Such openings may have benefit in determining the direction of blood flow in order to maximize left-to-right and minimize right to left flow especially in patients with combined left and right heart failure as occurs in patients with HFrEF. Similarly, an elongated hole such as a 1 mm wide slit with radiused ends may have low csa and shunting with low pressure differential and increased csa and shunting with higher pressure differential. The utility of such a design may have particular value with HFrEF patients.

Second the catheter may remove tissue. For example in creating a shaped aperture the catheter may utilize a cutting blade to cut the tissue from the septum and remove it from the body. Loose tissue removal is critical so that any loose tissue does not remain in the atria, creating a substantial risk of stroke due to embolization.

In either mechanism, the physician preferably engages the target tissue with a distal portion of the device, such as a tissue articulator. The tissue articulator may penetrate into or through the tissue, and then be actuated (e.g., via an actuator on the catheter or sheath handle) to hold the tissue and bring it to the cutting blade. Alternatively, the articulator may hold the tissue and the blade may approach it for cutting the tissue. Thus, the articulator works with the blade for one or more purposes, it may hold the tissue in place, guide the blade to the desired portion of the tissue, hold the catheter in place and on target, retain any loose tissue, or create an initial opening in the tissue for the device to pass into.

In a preferred embodiment, the tissue articulator, a portion of the tissue articulator or a distal capture component passes through the tissue as the catheter or sheath is advanced. Alternatively, an actuator, (e.g., an actuator on a handle, or simply a movable lumen/guide within the medical device) may be in or moved to a first position that advances or locates the tissue articulator forward away from the cutting blade. This advancement (or a separate advancement) may push the relevant distal component through the tissue. Once in place, either by actuation or mere advancement, the actuator is activated to a second position that causes the articulator or distal capture component to engage the tissue. The second position (or a third position) may also pull the tissue into a lumen in the catheter or sheath, tenting it so that a larger aperture may be cut.

In one embodiment the distal capture component is expandable. Once the expandable distal capture component has crossed the atrial septum it can be expanded. This may be accomplished a variety of ways, such as a bias toward the expanded position, but ideally the expansion is actuated by actuating an actuator component on the handle of the catheter. The actuator may be a knob, lever, trigger, etc., which releases a preshaped expandable distal capture component to expand, or forces the expansion of an expandable component into the desired shape. Ideally the expandable distal capture component is rigid, so when it is brought together with a proximal capture component, a high capture force can be placed on the tissue so the tissue does not easily pull out due to movements by the catheter, causing imperfect shunt size and shapes. The high capture force is preferably placed at the outer circumference, toward the proximal capture component, tightly pinching the tissue between the capture components. The distal capture component also holds high loading forces perpendicular to the capture, so when there is an in plane side load on the catheter the captured tissue does not pull out of the capture mechanism. The expandable distal capture mechanism has a very fine layer of mesh, braid, or solid material which traps all small tissue particulate to keep it from floating into the blood stream during the procedure.

The capture mechanism can capture the tissue by applying a preset force to hold the tissue. This preset force may be set by the physician. In one embodiment the physician sets the force before the procedure by adjusting the device. In another embodiment the device has settings or markings that allow the physician to control or adjust the degree of force, either pre procedure or during the procedure. In another embodiment the preset force is set during device manufacture. Alternatively the device may set a prescribed distance between or gap for the distal and proximal capture mechanisms.

Ideally, the proximal and distal capture mechanisms cooperate to capture the tissue without stretching it, and this is ideally done by capturing the tissue between them without moving the tissue substantially out of its original plane or location. Thus, in one embodiment the distal capture mechanism is first adjusted to the position of the distal side of the tissue, that is its grabbing surfaces in minimal contact with the tissue, and then the proximal side is brought to the proximal side of the tissue. These adjustments may be made by moving a shaft connected to the respective capture mechanism. The adjustments may also be made via an actuator. They may be manually controlled by the physician, or automatically controlled via a robotic or magnetic control system, for example. The two devices may be structured such that as they exit a retaining tube or catheter, they automatically expand. Thus, as the catheter passes through the septum in to the LA, it has a low profile. A first portion of the catheter e.g., an outer sheath, catheter, or tube, is then withdrawn, allowing the proximal tissue capture mechanism to expand. This mechanism is pulled or relocated to the surface of the tissue. The first catheter portion is then withdrawn further, while the proximal capture mechanism remains in place. As the first catheter portion withdraws, the distal capture mechanism may exit and likewise expand, automatically putting a clamp on the tissue, e.g., by its spacing from the distal portion.

In other embodiments the proximal side may be first advanced. In still other embodiments it is the physician's choice.

In addition, it is preferred that the capture mechanisms work to capture the tissue in its natural orientation, that is, not twisting or bending the tissue out of plane. Before the expanded distal capture mechanism is pulled proximal to capture tissue it is preferred that the catheter is aligned to trap the tissue in its natural orientation. First, the proximal capture component, as seen on fluoro or echo is advanced such that the must distal face of the proximal capture mechanism is touching the fossa ovalis in its natural plane. To improve visibility of the proximal capture component radiopaque and/or echolucent filler is added. This will allow an in plane capture and support the accurate shunt shape and size.

The proximal and distal capture mechanism can be fabricated from a single, or joining of two elastic, material(s) such as nitinol and retained for delivery. In such a form once the retained distal capture mechanism crosses the tissue, such as the septum, it may be released prior to, or in conjunction with, the proximal capture mechanism. The preformed shape and elastic nature of the material acts as an actuator and locking mechanism bringing the proximal and distal capture components in contact with the tissue to be capture with a prescribed capture force.

To optimize the shunt shape and size it is important to minimize the movement of the tissue capture point after device alignment, during capture and during cutting. This can be done by fixating the catheter at any point from proximal to distal. This is especially important after the catheter alignment just prior to capture. However, movement of the catheter after capture can still cause improper shunt shape and size if the loading force on the fossa ovalis tissue is sufficient to pull tissue from the capture point. Fixation of the catheter should control torque, advancement and withdrawal of the catheter relative to the catheter distal tip. The most efficient and safe way of performing this catheter fixation is to as solidly as possible attach the catheter outside the puncture site to the patient. One way to do this is to adhesively attach a catheter hub to the patient as close to the puncture site as possible. This catheter hub can securely grasp the catheter shaft or the catheter handle. If the patient moves the catheter hub and catheter will move with the patient, but the relative movement of the catheter distal tip with respect to the fossa ovalis will remain fixed. Alternatively, since the patient is sedated and generally does not move during the procedure, the proximal catheter shaft or handle can be fixed to the bedrail or similar, to fixate it and keep it from moving. To facilitate the latter the patient's leg can furthermore be fixated to the bedrail to keep movements minimized. The catheter can also be fixated by first fixating the introducer sheath with means already described, and then using a means to fixate the catheter shaft or handle to the introducer sheath.

After the catheter is fixated any remaining in-plane or longitudinal bias must be removed. The in-plane bias is a result of the catheter at the fossa ovalis crossing point being biased in-plane such that it slightly elongates the hole in the tissue which it is crossing through, as evidenced by high velocity blood jetting on doppler (TEE, TTE, ICE). The catheter shaft is aligned in the fossa ovalis plane such that jetting as seen on doppler is minimized. This is done by torquing the catheter shaft, and if not preshaped, also actuating pull wires to deflect the distal tip. By minimizing blood jetting alongside the catheter the shaft is brought into its original crossing point and in plane catheter shaft bias is removed. This will allow for a more accurate shunt shape and size.

Once the capture is completed using the capture actuator on the handle it is preferred, for safety and performance reasons, to not easily allow the capture to be released. For this reason a locking mechanism is preferably placed in the handle or in another part of the catheter so once the tissue capture is performed it is difficult to inadvertently release the tissue, or in some embodiments to release it without taking multiple steps. This will minimize any potential loss of cut tissue. To maximize accuracy of the shunt shape and size, as well as optimize safety, it is important to not allow any tissue to slip out of the capture system. To accomplish this while pressure can be evenly applied across the face of the tissue, it is ideal place all capture forces at the outer circumference of the capture mechanisms. Doing so prevents any edge from slipping out. This may be accomplished by having an outer raised knife like edge on the outer most perimeter of the distal portion of the proximal capture mechanism and something similar or complimentary on the proximal side of the distal capture mechanism, or vice versa. The diameter of these raised edge parts of the capture mechanisms should be just slightly less than the cutter blade. Also, to further improve capture teeth may be located on the raised edge. To maximize capture forces, without going beyond the strength of the catheter component, it is ideal to make the capture system spring loaded so a set range of capture forces will be obtained no matter the tissue thickness.

In one embodiment the physician will move the capture point slightly into the LA or the RA once the tissue is captured. For example, the catheter can have a component which, while activated, can move the capture point slightly into the LA, in a controlled manner. Alternatively, the physician can move the catheter, or an attachment point outside the body can be activated to move the entire catheter forward. This movement has two intended purposes. First, by moving the capture point slightly into the LA, the tissue is pulled slightly tight and over the blade, which helps facilitate an efficient cut. Secondly, if the tissue is tented slightly into the LA prior to cutting, as seen on fluoroscopy or echocardiography, the clinician will know when the cut is complete by watching for the tissue to collapse from its tented position to its natural plane. This tenting of tissue is only expected to require a few millimeters of movement of the capture point. The amount of advancement is preferably indicated on the catheter or its handle. This advancement or tenting into the LA is expected to be less than 1 cm. The advancement mechanism can also be used for final fine adjustment of the linear capture point just before cutting the tissue.

Once the mechanism is in place, the physician will use the cutting edge to create a durable interatrial shunt. In one embodiment the cutting blade is a circular blade. The circular blade, even when very sharp, is relatively safe. In an embodiment with no points on the blade, cutting the tissue requires significant force and/or slicing motion. In the preferred embodiment both force into the tissue and a slicing motion is applied. It is important to not have the blade move forward into the tissue without the appropriate amount of slicing or blade rotation. If there is too much forward motion relative to blade rotation and slicing, the forward motion may pull tissue out of the capture mechanism, either keeping the blade from effectively cutting or cutting the shunt with the wrong size or shape. To facilitate the precise forward travel of the blade into the tissue relative to the blades rotation a threaded component is used, so only one actuator controls advancement and rotation of the blade in precise coordination. The threaded component may be located anywhere in the catheter from the distal end to the handle. However, the preferred embodiment has the threaded component near or in the distal end of the catheter. There is also a blade stop incorporated into the catheter to keep the blade from advancing to far beyond the capture system and causing a safety issue. An indicator may show how far the blade has been advanced beyond the capture point and into the tissue.

This same basic catheter design may be implemented by energizing the metal cutting blade with RF cutting energy (or laser), such as that from a Valley Labs™ generator. In this application blade rotation or tissue slicing is not necessary. However, blade advancement must be coordinated with the application of RF energy. In addition, it is preferred that the RF energy be focused on the tissue. As such, if a shaped blade is used, e.g., circular shaped blade 16, the majority of the blade may be coated to reduce the portion that emits RF energy. For example, the shaped blade may be coated with an insulator from the proximal portion to just short of the distal portion, leaving only the distal circular edge uncoated, and available to emit RF energy into the tissue. The blade may be blunt in this scenario. While a sharper blade may work with the RF to penetrate, it is not necessary in other embodiments. In addition, the blade may be in electrically isolated portions, such that one portion may be energized at a time, with each portion being on a different electrical pole. When using an RF blade, it may be advantageous to have the return electrode be a patch on the outside of the body. It may be preferred that the return electrode be on the catheter. For example, the distal tissue capture mechanism may include one or more return electrodes. The outer edge of the distal tissue capture mechanism may serve as return electrodes, providing a very controlled path for the RF energy. If the return electrodes are divided into electrically isolated portions, the device may have the ability to sequentially direct the RF energy from one portion of the blade to different portions of the return, or to target a specific portion of the tissue 30.

The guidewire, or a navigation electrode, or an electrode on the shaft for the distal tissue capture mechanism are all locations for potential return electrodes.

In one embodiment the blade locks into the advanced position and acts as a capture component, keeping tissue from releasing as the catheter is retracted, by holding the tissue, and all or part of the distal and proximal tissue capture components inside a cavity in the blade. With the blade locked in the advanced position the blade could cut into tissue if the system is advanced during the catheter retraction processes. To protect against the accidental cutting the expandable distal capture mechanism is sufficiently long so it protects tissue from unintended cutting from the blade. In addition, OD of the distal capture mechanism has an OD which is close to the ID or cutting edge of the blade, making unintended cutting unlikely.

For proper utility in patients who need transeptal shunting of blood it is critical that the aperture be "durable" such that it will stay open for a long period of time and even permanently, as defined below. The shunt size can be titrated by measuring the left atrial pressure either at rest or with exercise. Likewise, the doctor can measure oxygen saturation in the right atrium, or cardiac output. The medical device of the present invention preferably includes means to measure pressure and/or oxygen saturation, such as a sensor or via fluid removal for testing.

In one version of the procedure, the device or a complementary device/device portion crosses the septum into the left atrium and records the resting pressure (or with exercise). At this point the durable aperture is cut as detailed elsewhere. Then, the pressure measurement is again performed and it is determined if the aperture is sufficient. One advantage of the present procedure and device is the ability to measure success during the procedure, and adjust the shunt size as needed, rather than waiting until post procedure and having to reenter the patient.

In certain patients it is preferred that the hole be at least 3 to 12 mm, preferably 4 to 10 mm, or 6 to 8 mm, in diameter for the desired clinical benefit. In other patients a higher pressure may indicate that a smaller aperture be formed, e.g., 0.5 to 5 mm, or 2-3 mm. However, such small hole sizes have increased risks of closing, tissue healing, and plugging, and are accordingly unlikely to be a aperture absent exceptional circumstances. The interatrial shunt lowers LA pressure especially during exercise in heart failure patients. The left-to-right shunting can cause a decrease in left ventricular (LV) CO and an increase in right ventricular CO. The reduction in LA pressure, however, might allow patients to achieve a higher level of exertion leading to higher heart rate and thus an increase in LV CO. Furthermore, increases in RA pressure and pulmonary arterial pressure can occur, but in HF patients, despite the increase in RV CO, a reduction in pulmonary venous pressure can actually occur. The size of the shunt can determine the extent of all these hemodynamic effects, and enable a Qp/Qs ratio sufficient to reduce LA pressure without RV overload. The clinically necessary size will vary from patient to patient. Subsequent to the procedure the physician will monitor the patient at one month, three-month, and six-month exams to determine if the size of the hole has shrunk. While it is anticipated that healing tissue may slightly shrink the aperture on the order of 1 to 2 mm, if the aperture remains open at six months it is considered "permanent" or durable for purposes herein. It is also desirable that the aperture be visible on an echocardiogram so that it can be readily measured. Ultimately, for these patients, safety and a proper balance of blood hemodynamics, oxygenation will be used determine the aperture size, shape and quantity.

The tissue may be removed by a device using, for example, suction or grasping mechanisms. In a preferred embodiment the catheter, e.g., the tissue articulator, will pull the tissue into the blade to positively retain it and keep it from releasing into the heart. In addition to its utility for tissue removal, the suction and grasping mechanisms may also be extremely useful for positioning the device, and retaining the device in the desired position during operation. Additionally, suction may aid in determining that the blade is orthogonal to the tissue, e.g., that it has the proper orientation for cutting. For example, if under light suction in the blade's lumen a seal is formed between the blade and the tissue, the blade may be determined to be at a proper orientation to the tissue for cutting a durable aperture. Likewise, sensors on the grasping mechanism may be able to determine how far into the tissue the grasping mechanism is. If four hooks, for example, all 90 degrees apart, have penetrated the tissue to the same depth, it may be determined that the device is orthogonal to the tissue.

Creating a hole in the heart without leaving behind an implant avoids the need for anticoagulant therapy, lowers the risk of infection, and avoids the use of an implant that may come loose over time. In addition the procedure is substantially simpler than installing and leaving behind an implant. Due to the lack of an implant, there are no risks of MRI compatibility, no risk of device failure or fracture. It is easier to close the aperture if needed absent a device, and the overall total cost of care is lower. No implant means faster and safer crossing of the septum during future catheter based surgical procedures, such as treating atrial fibrillation or ventricular tachycardia. Finally, the procedure is faster and will allow for a more efficient use of hospital facilities and physician time.

There are multiple ways to determine if the aperture is large enough to be efficacious. Subsequent to the procedure the physician may do so by, e.g., examining the aperture on an echocardiogram visually and using doppler, calculating the degree of shunting, performing an exercise tolerance procedure, by measuring the ejection fraction, by measuring the wedge pressure, oxygen saturation, or other means. It is preferred that a clinical evaluation be conducted such as a walking test, to determine the practical effect on the patient. The invention allows for easier adjustment of aperture size compared to similar solutions. In particular, if the aperture size is too small, an additional aperture may be created, or the existing aperture can be expanded. Because certain clinical evaluations can be performed immediately after the patient is first treated, it may be possible in many cases to leave the catheter in place during the evaluation, use the same catheter to create the second aperture or increase the size of the existing aperture, and thereby avoid a second procedure. This determination can be performed by having the patient exercise using upper body exercise devices and measuring the LA pressure prior to and during exercise. If the reduction is not sufficient to reduce PCWP then a second hole can be created and the exercise evaluation repeated. This is not possible with the prior art devices.

The invention can be used to create shunts from other high pressure to low pressure regions with the potential of creating similar therapeutic benefits. An example of this is the creation of a shunt from the right atrium of the heart to the pulmonary artery. In this instance, there is an advantage over a shunt between the right and left atrium because a shunt between the right atrium and pulmonary artery does not waist oxygenated blood and has a lower risk of right sided blood entering the left side of the heart. Yet another way to create a decompression of the left side of the heart may be to create a shunt in a tricuspid leaflet. These are only possible examples of how a shunt creating catheter may be used in a minimally invasive way to prescriptively adjust pressures in the heart as a medical therapy.

Also disclosed is a medical device for creating the aperture between the left atrial chamber and the right atrial chamber. The medical devices have dimensional requirements depending on several factors. First, the length of the device will depend on its point of entry. For example, a catheter that will be used in a percutaneous entry at the femoral vein and which must reach to the right atrium will typically be at least 120 cm long and more preferably 140 cm. A catheter that will enter the body at a different location in many cases will be substantially shorter. The more lengthy and torturous the path the catheter must take, the stiffer the catheter body may need to be, and the more likely the catheter will be to require stiffening elements such as a stainless steel or nitinol braid. The need for a stiffer catheter is particularly acute for the present device. It must first take a long path through the body to the right atrium, then turn at a sharp angle to address the interatrial septum, and then project enough force along that turn to push the cutter through the interatrial septum. It is difficult to project that force along the length of the catheter body, which runs from the groin region to the heart, and then successfully get the force to take the turn toward the septum without first pushing the catheter higher inside the heart rather than to the side toward the septum. Accordingly, unlike many prior art surgical catheters, the present device may require a substantially stiffer body, provided by braiding, nitinol stiffening devices, or multiple catheter layers. Another reason for a stiff catheter is, in combination with ridged proximal handle/end fixation (bed rail), the clinician can make fine (submillimeter) movements to the distal tip with respect to the tissue.

Typically a thinner catheter is preferred, so long as the cutting elements are sufficiently sized to create a large enough interatrial aperture. For example, it would be preferred to have a catheter shaft of nine French. However there is always a trade-off between a small diameter device and the need to create a sufficiently sized interatrial aperture. Thus it may be advantageous to have a small diameter shaft for the bulk of the catheter length combined with a somewhat larger distal working end on the catheter, or an expandable distal working end that has a small diameter upon insertion to the vein and can be expanded once in the right atrium and then collapse back to a smaller diameter for removal through the vein. On the proximal end of the catheter it is advantageous to have an easily manipulable handle so that the physician can direct the catheter into its desired location and control the cutting device. It is also advantageous to have a hub outside the body to secure the system in place during portions of the procedure.

With reference to FIG. 1, the catheter 10 comprises an elongated catheter shaft 12 having a distal end 14 and a proximal end 15. Proximal end 15 includes a handle 18. The handle 18 comprises a first actuator 20 and a second actuator 22. Handle 18 further includes a fluid port 24 and an electrical connection (not shown). Handle 18 may include additional actuators, and may be sized to fit within a catheter hub for securing catheter 10 in a position. Catheter 10 may further include pull wires attached to an actuator for actuating distal elements, moving a lumen or shaft, steering, or the like. Catheter 10 may be pre-curved or pre-bent such that it will automatically orient towards the interatrial septum once it reaches the right atrium.

It may further include irrigation ports and the like. Catheter 10 further includes radiopaque markers 26 in a designed pattern that allows the physician to determine the location and orientation of the catheter 10 in the patient and the orientation of the different components of the device relatively to each other. Catheter 10 may further include ultrasound markers 28 again in a designed pattern such that the physician may locate the catheter 10 in the patient on ultrasound imaging. Of course any catheter or system portion described herein may use any one or combination of markers, such as radiopaque, ultrasound, electrodes, magnetic sensors, or visualization systems to determine the location of the catheter or system portion in the body or with respect to another portion of the system.

The elongated catheter shaft 12 is preferably hollow, having a lumen 13 that has the ability to pass a guidewire 40 through it. Catheter 10 is designed to work in conjunction with an introducer 50. Introducer 50 may either extend the entire length from the percutaneous incision to the left atrium of the heart, or may only cover a portion of catheter 10.

The distal end 14 of catheter 10 comprises a cutting means 16. In a first embodiment the cutting means 16 is a razor like member formed of steel or another suitable metal or material adapted to cut a thin tissue. Toward this end the cutting means may be very thin so that it cleanly and easily pierces the thin tissue. In those embodiments where cutting means 16 has a sharp edge exposed at the end of the catheter 10, one preferred embodiment uses introducer 50 to cover and protect the vein and other tissue from the cutting means 16 until the catheter 10 is delivered in place and actuated by the physician to cut the target tissue. In FIG. 1 the cutting blade 10 has a sharp edge on its outer diameter. In a preferred embodiment the cutting edge may be on the inner diameter, and thus may sit flush with internal catheter elements such as shaft 12, or tissue articulator or dilator 60 (tissue articulator 60 shown in FIG. 1A). As shown in FIG. 2, in an embodiment where the cutting edge is on the ID of cutting means 16, and rides over dilator 60 it is preferred that the OD of dilator 60 have a diameter just slightly smaller than the ID of cutting means 16, such that the dilator protects the tissue from the blade edge. In other embodiments a cone (not pictured) or other distal element may cover or sit flush with the cutting blade 16 so that the blade is protected until actuation. The device may use a retractable outer blade protector that is slightly larger than and/or in front of the blade. The retraction may occur when actuated at the handle, when the sheath is withdrawn (or the catheter exits the sheath), when the device is bent toward the fossa, when the tissue articulator, dilator, or other distal component advances, or the like. For example, the dilator 60 may be on a first shaft (not shown). The cutting means 16 is then on a second shaft (not shown), that has a lumen. Inside the lumen of the second shaft is the first shaft for the dilator. The second shaft in turn is inside the lumen of shaft 12. The shafts may be rotatable and movable with respect to each other, either manually or by an actuation. In one embodiment the second shaft is highly torqueable, so that the cutting means 16 may be rotated as it cuts.

The cutting means 16 may be a serrated blade which will allow for a lower cutting force. Likewise the cutting means 16 may comprise a vibrating blade to likewise allow for a lower cutting force. Alternatively, the cutting means 16 may be on a torque shaft 12 that allows the cutting means to be rotated, and preferably rotated and controllably advanced to cut the tissue 30. The control between the blade rotation and distal advancement may be controlled by a thread or similar mechanism such that the tissue slicing happens at a predictable speed, to optimize the tissue cutting.

As depicted in FIG. 1, the shaft 12 may extend to the tip of the cutter 16. It may also extend farther, and be designed to pass through to the LA. Finally, it may terminate proximally of the cutting surface, proximally of the entire cutter, or at some other location depending on the design and workflow of the system. The cutter may also be constructed to move along the shaft 12, such that upon actuation or release, the cutter moves forward to engage the tissue 30.

The introducer 50 is typically a hollow sheath. Introducer 50 may include braiding along the outer cylinder to provide stiffening. Introducer 50 may further include a handle at the proximal end, an actuator, and pull wires attached to the actuator for steering, irrigation ports and the like. In particular, pull wires may be strongly advantageous. Unlike prior art devices which create a hole by energy sources or by implanting a device, the present device may find that significant pressure on the cutting blade 16 is necessary. Accordingly, in a preferred embodiment the sheath wall, and/or the catheter wall are braided or reinforced to provide a stiffer device. The lumen of introducer 50 must have an inside diameter sufficiently large to accommodate the outer diameter of the shunt cutting catheter end, which may be substantially larger than the OD of the rest of the catheter shaft 12. In some cases only a portion of introducer 50's lumen is large enough to accommodate the distal end 14, with the remainder of the introducer being narrower to allow easier navigation through the vein. In these cases the catheter 10 may enter the body already in the introducer 50, with its widest portion prepositioned in the wider portion of the introducer 50. In other cases the introducer's 50 entire lumen must be wide enough to accommodate the catheter's largest OD, e.g., when it is positioned in the body first.

Likewise, because the pressure must be transmitted from the length of the introducer or catheter, that pressure will initially, push the cutting edge and the entire catheter along rather than through the septum. For example, in a femoral vein entry procedure, the catheter is initially pushed upwards rather than towards the left atrium. Providing stability and steerability in either the introducer or the catheter may greatly reduce this upward pressure and redirect the force towards the interatrial septum 30 to provide a proper cut.

Likewise, providing anchoring means or stabilizing means can prevent the catheter and the cutting blade from shifting and allow a clean cut in the desired location. Thus, in one embodiment the assembly further includes an anchor. The anchor can be an in vivo, such as a component at the end of the catheter that hold the catheter in place. For example, hooks, corkscrews, or a forceps may hold the tissue tightly. Alternatively, the balloon, pigtail, or other tissue retention means described herein may serve as an anchor.

In another embodiment the anchoring mechanism is outside the body. Thus, the anchor can attach to the patient's exterior or the patient's bedside and hold the proximal portion of the catheter securely, e.g., a handle brace or catheter hub that attaches to the patient's bedside. In another embodiment a robotic system provides the anchoring mechanism by securely holding the catheter or handle. Of course, multiple anchoring means may be employed. An anchor is important because very precise control of the catheter and the cutting means are important for safe and successful procedures. Placing the cutting means in the wrong location or making it cut at the wrong angle results in a much more difficult cut, or a less safe cut as the cutting means may perforate the atrial wall on the other side of the septum. Thus, it is advantageous to have movement control down to the 1 mm level. Of course, providing a visualization system that has a similar resolution provides a synergistic effect with having a high degree of movement control.

In another embodiment the assembly further includes an orthogonal guide, the orthogonal guide adapted to hold the shaped blade in an orthogonal position to the interatrial septum.

Introducer 50 further includes radiopaque markers 26 in a designed pattern that allows the physician to determine the location and orientation of the introducer 50 in the patient. Introducer 50 may further include ultrasound markers 28 again in a designed pattern such that the physician may locate the introducer 50 in the patient on ultrasound imaging. Preferably, the radiopaque markers 26 and ultrasound markers 28 on the catheter and introducer are distinguishable from each other and accordingly the physician is able to determine which markers are on the catheter in which markers are on the introducer readily such that the physician is able to determine the spatial relationship of the two devices, the catheter 10 and the introducer 50.

This spatial relationship allows the physician is to determine when the catheter 10 exits the introducer 50 and the cutting mechanism 16 is active, as well as determine the location and orientations of the devices at all times.

In one embodiment, in operation the introducer 50 is positioned next to or near a target tissue 30. Specifically the introducer 50 is located near the interatrial septum. The introducer 50 may be so located through a physician's experience touch and feel, or using the markers 26, 28 in conjunction with imaging system. Other location systems are possible, including MRI, electroanatomical navigation systems such as EnSite®, Carto®, or MediGuide® systems, along with the corresponding sensors on the introducer 50 and catheter 10. The sensors 26, 28, or sensors that work with other imaging systems, may advantageously be located at the tip of the sheath or the catheter. In this embodiment the sensors may identify on a visualization system when the sheath is orthogonal to the tissue 30. Likewise, electrodes, pressure sensors, fiber optics, a camera, or the like may sense the tissue contact or proximity, and may thus identify when the sheath is in contact with the tissue, and also when it is orthogonal to the tissue. In such a case it may be advantageous to have two such sensors 180 degrees apart, or preferably 4 or more sensors 90 degrees apart. In another embodiment a precurved sheath 50 will terminate before reaching the target tissue, but will direct the catheter toward the target tissue, such that pushing the catheter shaft 12 forward will not advance the distal catheter tip upwards, but will direct it toward the left atrium. The sheath 50 may be locked in place outside the body independently of the catheter 10, and thus may be held in position while the catheter is further advanced.

While proper alignment of the catheter or sheath is discussed above, and is important in most embodiments, it is understood that in those embodiments the alignment of the sheath with the tissue is important primarily to align the cutter with the tissue so that the shape, location, and size of the aperture can be controlled. However, it is most critical that the blade be aligned properly with the tissue, and in some embodiments the face of the blade may not be orthogonal to the sheath or catheter. In fact, in one embodiment the blade is at a 45 degree angle to the longitudinal axis of the catheter. As such, the catheter (or sheath, guidewire) need not be bent at an orthogonal angle to the tissue, but indeed may remain straighter as the blade itself will provide the proper orientation. Of course, the adjustment of the angle to fit the needs of the cut and the device is expected. In other embodiments the tissue is brought into alignment with the cutter, that is, the tissue is held by the tissue retention device and turned to face the cutter.

Once the introducer is in position (such as next to or near the target tissue 30, or on the other side of the RA) the catheter 10 is advanced past the end of or to the end of the introducer 50 and placed in contact with the tissue 30. Preferably using the unique markers 26, 28 the physician can tell on the visualization system when the catheter has exited the introducer or has contacted the tissue. Likewise, the catheter 10 may include sensors (not shown) that identify when it contacts the tissue, such as a force sensor, fiber optics, a camera, and electrode using impedance sensing, mapping systems, ultrasound, or the like. In a first embodiment, the circular cutter 16 is advanced into the tissue 30 to cut a circular aperture in the tissue. In an alternative embodiment the introducer 50 is not utilized and the catheter itself is steered into position near tissue 30, and is advanced to cut the aperture.

In one embodiment, once the introducer is in place a transeptal crossing system is used to cross the fossa, as detailed above. Then once across the crossing system is typically replaced with a guidewire. The guidewire 40 remains in position across the interatrial septum and guides either some or all of the introducer 50, the catheter 10, the dilator, a tissue articulator or a tissue capture mechanism into position. Guidewire 40 may comprise a retention means on its distal end. Alternatively, guidewire 40 or the retention means may be a part of catheter 10. For example guidewire 40 may include a balloon 42, a pigtail (not shown), an expandable nitinol basket (not shown), a disk or expandable disk (not shown) or similar means. In operation the guidewire 40 is passed through the interatrial septum. Once across, balloon 42 is inflated (or the pigtail secured or the nitinol basket or the disk expanded) and the guidewire is pulled proximally towards catheter 10 to secure the tissue against catheter 10 and cutter 16. Likewise a pigtail, hook or helical means can be utilized to secure the tissue against catheter 10. Multiple means may be used, including a balloon 42 to push the tissue and a hook to retain any loose or dislodged tissue.

While the balloon, pigtail, or similar means are shown as being on the distal portion of guidewire 40, they may also be on the distal portion of the catheter 10. For example a thinner, distal portion of catheter 10 may be passed through the interatrial septum 30 to allow the balloon 42, or pigtail to secure the tissue 30. The distal portion of the catheter with the articulator, e.g., balloon 42, pigtail, basket, or disk may ride over a guidewire, or may forego a guidewire entirely. In such an embodiment the catheter 10 may not need lumen 13, or may find alternative usage for it, such as irrigation or suction. Of course a lumen 13 for a guidewire 40 may still use the lumen 13 for irrigation and suction as well.

In an embodiment the articulator (balloon 42, pigtail, basket, or disk) will pull the tissue of the interatrial septum into a lumen 32 of catheter 10 such that the tissue is tented, preferably into the catheter's lumen (as shown). Once the tissue is tented the cutter 16 will cut the tissue 30 resulting in a larger aperture due to the tenting. Tenting the tissue has several advantages. First in many cases it will allow for a larger aperture size combined with a smaller catheter size. Likewise it may give the physician a degree of control over the size the aperture. For example if the physician desires a smaller aperture for a particular patient, he may wish to reduce the amount of tenting or keep it to a minimum. If the physician desires a larger aperture for the patient he will increase the amount of tenting pulling the tissue further into the lumen 32 creating a larger aperture when the cutting means 16 is applied.

While the above description describes guidewire 40 as a separate device, it is also contemplated that catheter 10 may comprise a lumen in its center containing the guidewire 40. In this embodiment guidewire 40 is first advanced across the interatrial septum, either by itself, piercing the septum, or over a pre-existing guidewire placed earlier in the procedure. The guidewire 40 may be actuated by the first or second actuator 20, 22 on handle 11, manually by the physician, or by an actuator on a separate handle.

In another embodiment guidewire 40 is replaced by an RF tip or needle on the dilator 60 (FIG. 1A) that will penetrate tissue 30 and allow the dilator 60 to enter the tissue.

In one embodiment the handle 11 comprises a sliding actuator that advances the guidewire distally or withdraws it approximately in a one-to-one ratio between the movement of the guidewire and the movement of the actuator on the handle. In this situation once the catheter is advanced to the interatrial septum and the guidewire 40 is advanced across the septum, the balloon is inflated, and pulled back against the tissue 30 by actuation or by withdrawing the entire device. At this point the actuator 20 is moved proximally to pull the tissue into the cutter 16 creating the aperture in the tissue 30. In another embodiment the guidewire 40 terminates proximally of the catheter 10, and is manipulated entirely separately, either by hand or by its own actuator.

The device preferably includes one or more tissue retention means. In FIG. 1, the guidewire may include a pigtail or hook, and as a result the tissue cut from the interatrial septum to complete the aperture is positively retained the inside the catheter 10 and is withdrawn from the body with the catheter 10. While the guidewire has been described as having either a balloon or pigtail, other articulation and tissue retention devices are contemplated. In particular a disc device can be utilized (not shown). The disc device may include one disc that is navigated to the distal side of tissue 30, or may include a disc on each side of the tissue 30. The two discs may be actuated to secure the tissue between them. The disc may be expandable having a small diameter when crossing the septum and a larger diameter when securing the tissue. The disks may present a flat face to the tissue 30. Alternatively, the disks may be cones, concave, or convex, such that they effectively put all pressure along specific portions of the tissue, e.g., an outside edge of the tissue portion to be cut. Cutter 16 may ride over the disc(s), pulling them into lumen 32 to cut the tissue which then remains retained between the two discs and is removed from the body. In particular, in a preferred embodiment the device may include both proximal and distal tissue retention devices, of the types described in more detail throughout this application. The tissue retention devices described above and below may be mixed and matched. For example, a distal disc described above may be combined with proximal hooks or suction (below). One portion may be connected to one portion of the system, e.g., the proximal hooks may be attached to sheath 50 or catheter 10, while another portion, e.g., the distal disc or the balloon 42 may be attached to a different portion of the system, e.g., guidewire 40, tissue articulator 60, or catheter 10, or have its own shaft.

Figure 5:
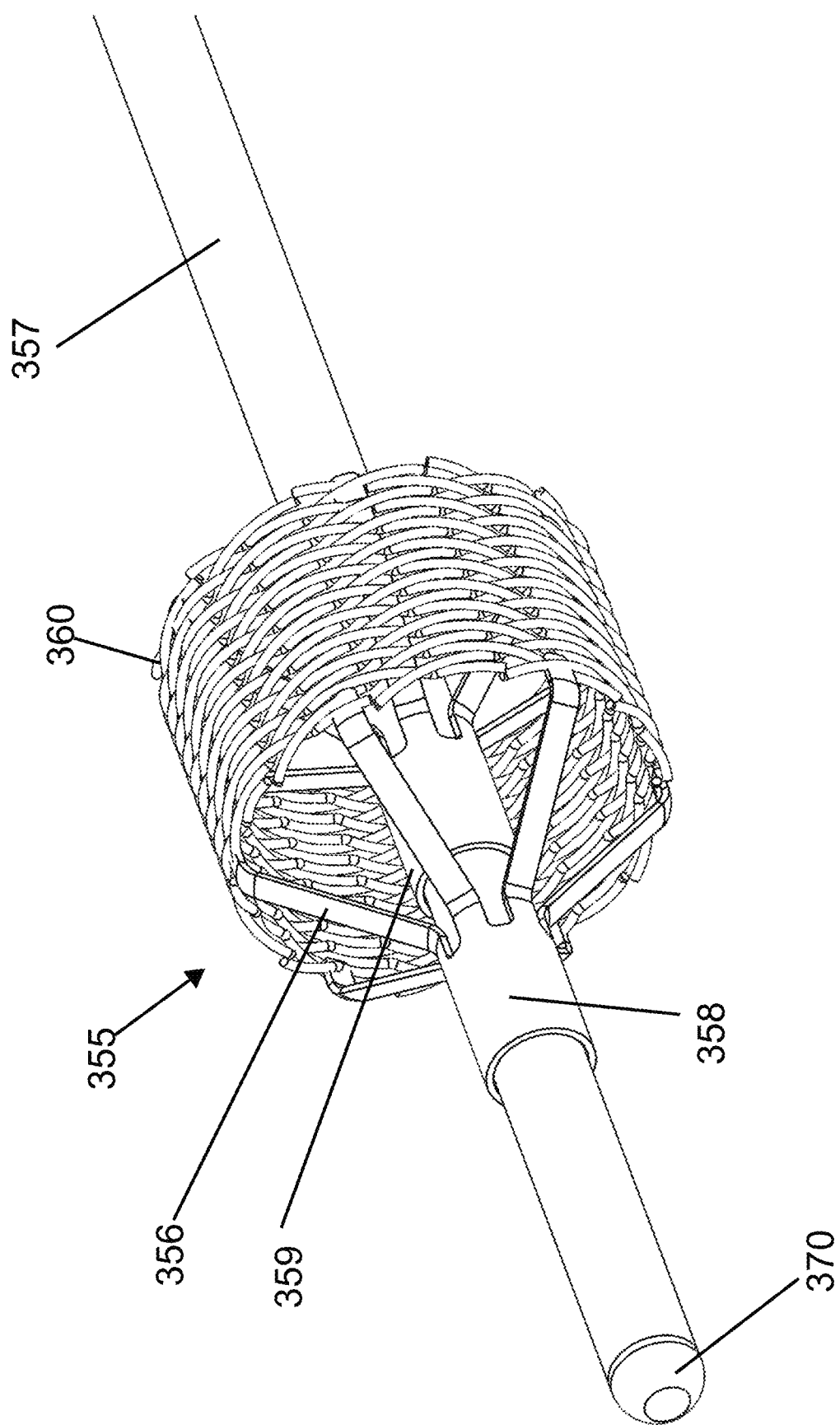
FIG. 5 is a partial perspective view of a tissue capture mechanism constructed according to the present disclosure.
Figure 5B:
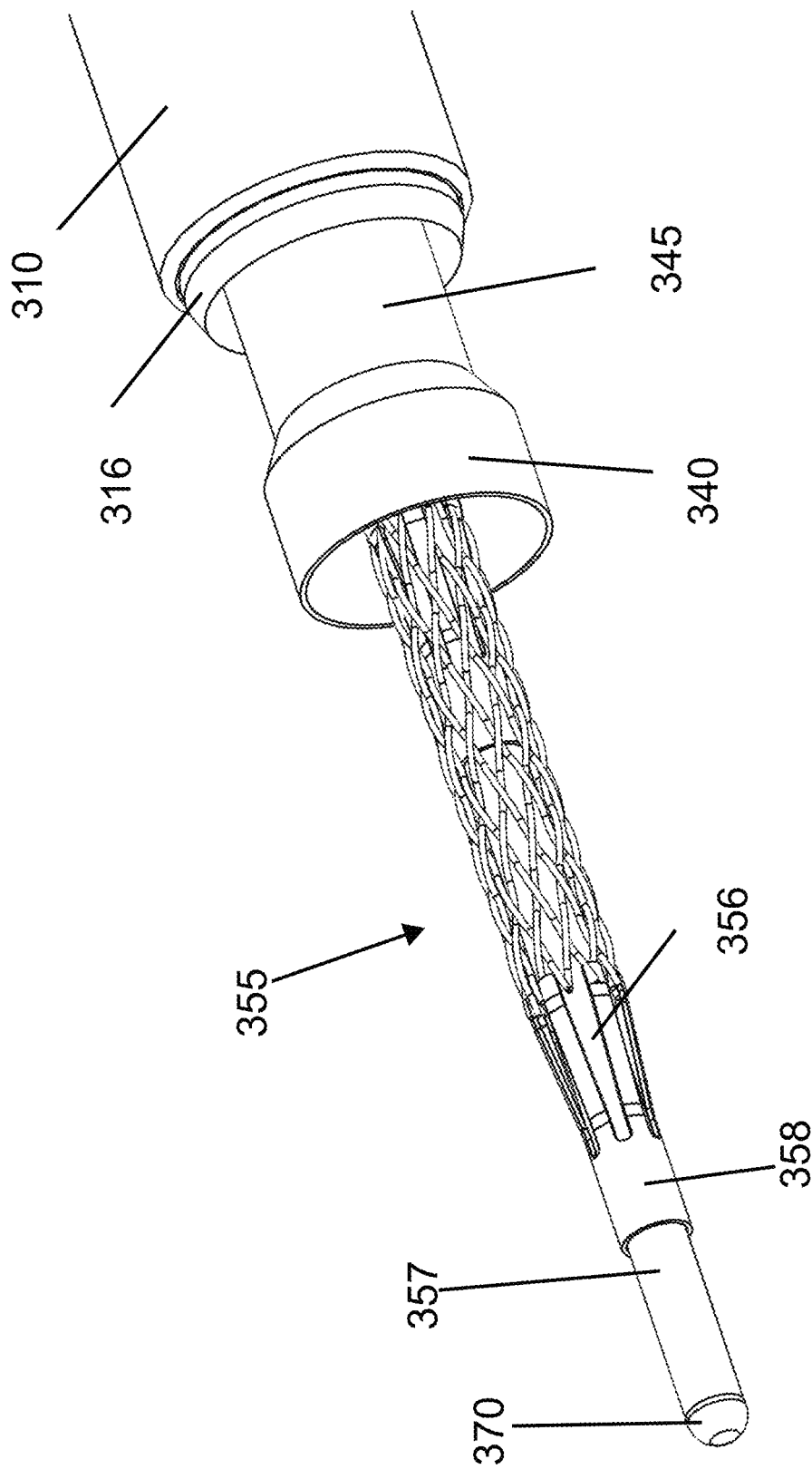
FIG. 5B is a partial perspective view of a distal catheter portion and tissue capture mechanisms constructed according to the present disclosure.

As shown in FIG. 5 and FIG. 5B, in one embodiment a tissue retention device 355 consists of a shaft 357 with a distal tip 370. Distal tip 370 may be atraumatic, and may have a lumen exit for a guidewire. A nitinol structure, such as wire braided cylinder 355 or basket 355 may be connected to shaft 357 by struts 356. Some or all of struts 356 are connected to the shaft 357 by a laterally movable collar 358. While the tissue retention device is within the catheter 10 or sheath 50, or a retention sleeve (not pictured) in one embodiment the collar 358 is moved to its most distal location, pulling struts 356 down to lie closely on top of shaft 357, as shown in FIG. 5B. Doing so pulls weave 360 inward to likewise lie closely on top of struts 356, substantially reducing the diameter of the tissue retention device for delivery through the vein to the RA. In one embodiment, a sleeve (not shown) remains over the basket 355 to keep it in the withdrawn position, until the device crosses the septum to the LA, at which point the sleeve is withdrawn, or the shaft 357 and basket 355 are further advanced to exit the sleeve. When collar 358 is moved to its proximal position, e.g., via actuation or via biasing, the struts push away from the shaft 357, and weave 360 expands, creating a large surface area. The tissue retention device may have one collar, or it may have proximal 359 and distal 358 collars, one of which or both being slidable with respect to the shaft 357, and each other. When the collars 358 and 359 are pulled apart (via actuation or biasing) the weave is contracted. When they are pulled together, the weave is expanded.

The expandable distal devices disclosed herein may rely on a button or certain mechanism to force them open (nominally closed), or rely on some type of containment tube/system, that when released, they open by themselves (nominally open). The latter is preferred though, so it fails open and does not loose tissue.

The tissue retention device may be set to be nominally open, that is, when it is not constrained it returns to or stays in an open state. This can be a preferred fail safe, as the device can still be pulled through the fossa ovalis in its open state, but will retain any tissue. For example, the struts 356 and basket 355 may be formed of nitinol in its open state. In this embodiment, the device may be stored in an open state, and an early step in the procedure is to contract the basket 355 and place it inside a sleeve, tube, or catheter (not pictured) that will hold it in its contracted position.

The tissue retention device in operation is advanced through the tissue to the distal tissue side, and then activated, either by an actuator on the handle, by naturally expanding on exit from sheath 50 or catheter 10, by removal of or from the sleeve (not shown) or a similar means. If a sleeve or tube is used to constrain the basket 355, it is preferred that the sleeve cross into the LA, for example, 1 mm across, before its advance is stopped and the basket 355 is removed for expansion. While the sleeve, tube, or catheter that constrains basket 355 could stop in the RA, and the basket 355 could be further constrained from expansion by the fossa ovalis as it crosses, or begin its expansion as it crosses the fossa ovalis, it is preferred that it remain at least partially constricted, if not fully, as it crosses into the LA by the sleeve or by an actuator.

In another embodiment the basket 355 is formed of a readily deformable material, such as stainless steel. In this embodiment it is delivered in its constricted or reduced form, as shown in FIG. 5B, and is nominally closed. That is, it is biased to be closed, or reduced to a smaller diameter, during delivery, as shown in FIG. 5B. At the desired location (e.g., in the LA if a distal tissue capture mechanism, or in the RA if a proximal tissue capture mechanism), it is actuated and deformed to an open, or larger form as shown in FIG. 5. Because the stainless can be deformed from one shape to another, once actuated the basket 355 is now nominally open. If any constraint is removed, it remains in the open position as a failsafe.

It is then positioned, as described above, on the distal side of tissue 30. As shown in FIG. 5, the tissue retention device 355 has several advantages. A reduced diameter while collapsed allows easy and safe transseptal crossings, with minimal tissue damage. The increased opened diameter allows a large tissue area to be captured. In addition, the design of the tissue retention device 355 allows all of the devices retention force to be placed along the outer edge of the tissue portion to be cut, providing a more certain retention of the tissue while avoiding sliding or movement of the tissue during or prior to cutting. The diameter of the distal tissue retention device 355 preferably matches or is complimentary of the diameter of the proximal tissue retention device 340, on shaft 345. Because they are on separate shafts, the proximal and distal tissue retention devices may be advanced, withdrawn, or actuated independently of each other and the cutter 316 and the catheter 310.

As drawn for the sake of illustration, tissue retention device 355 appears open at its distal end. However, to ensure tissue retention, the device 355 may have a tissue trap or a sealing material, e.g., a fine mesh on the distal end to retain any tissue portions that come loose. The expanded size of the tissue retention device ideally matches any tissue retention device on the other side of the tissue, such that one either fits neatly inside the other to hold the tissue, or that their diameters match, and are just slightly smaller than that of the cutter 16.

As shown in FIGS. 5 and 5B, basket 355 may be conical in shape. It may also take on a tapered shape, e.g., a cone or elongated cone with a narrower distal portion. In such an embodiment it may serve as a dilator for navigation through the body. The weave may be tight enough that the tapered cone may serve as a tissue trap, or another material may serve as a tissue trap.

Figure 6A:
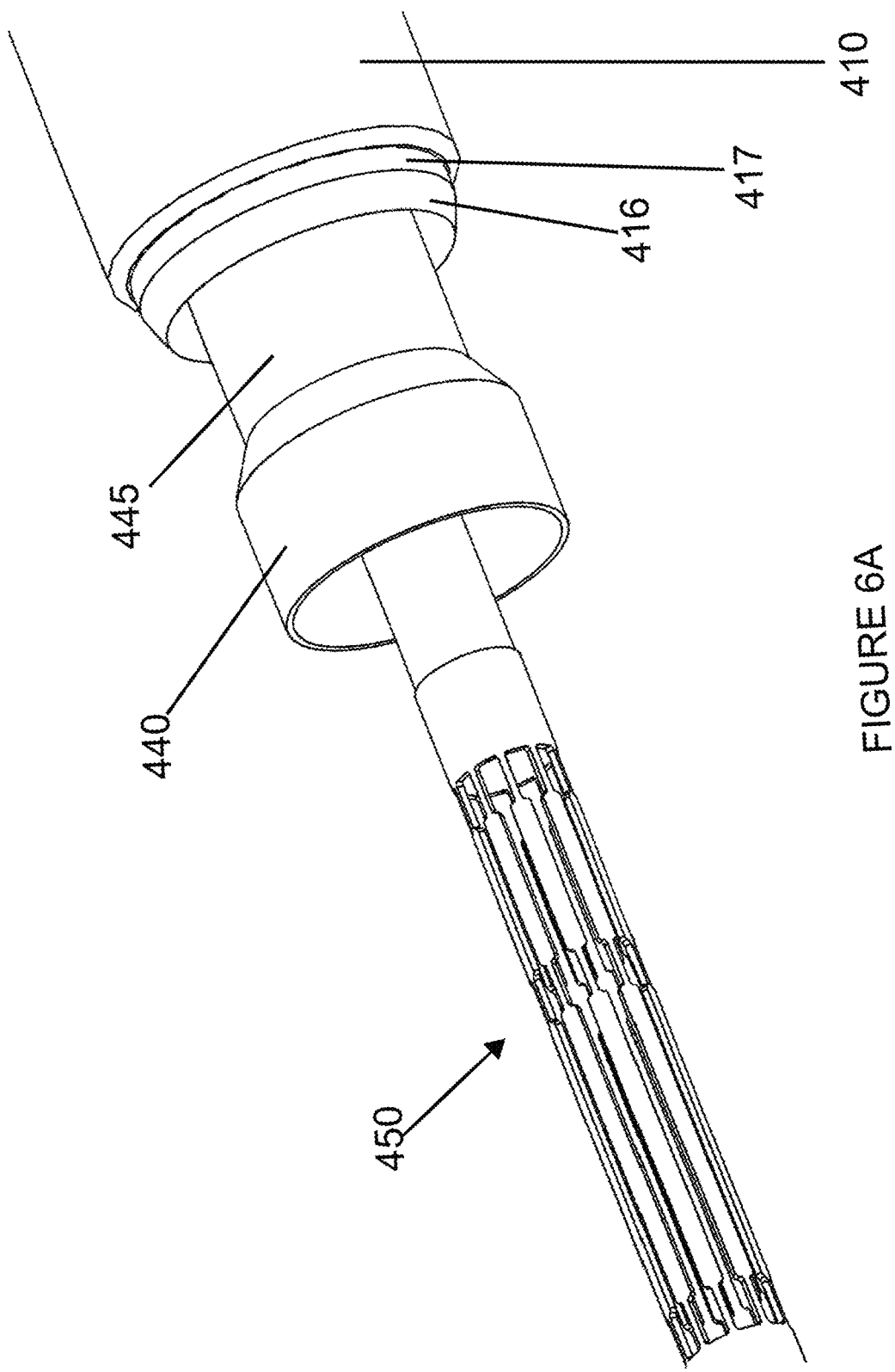
FIG. 6A is a partial perspective view of a distal catheter portion and tissue capture mechanisms constructed according to the present disclosure.
Figure 6B:
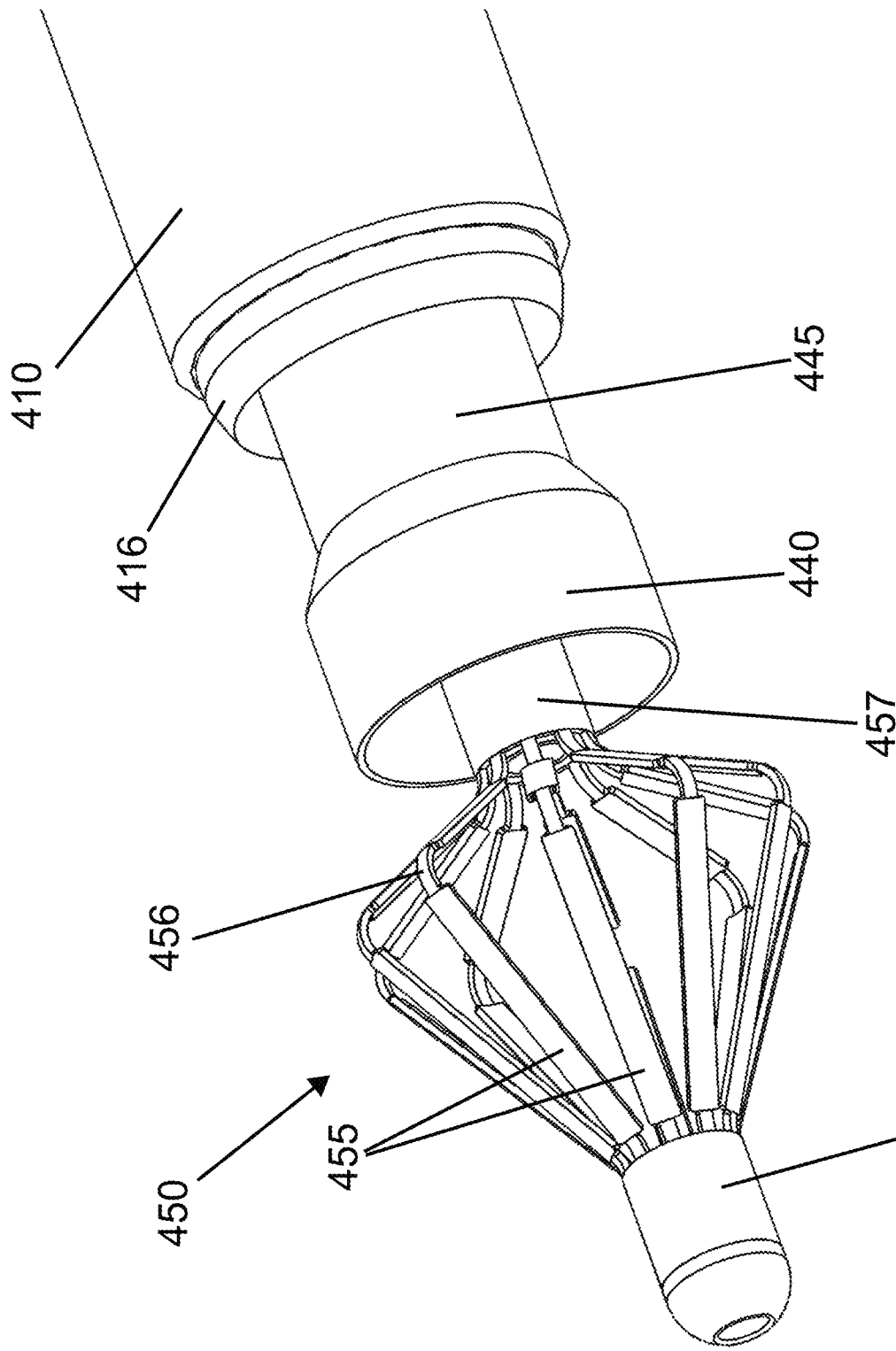
FIG. 6B is a partial perspective view of a distal catheter portion and tissue capture mechanisms constructed according to the present disclosure.

As shown in FIGS. 6A and 6B an expandable tissue retention device 450 may consist of struts 455, with bend 456. In one embodiment, during delivery into the body, tissue retention device 450 lies flat on its shaft, as shown in FIG. 6A. In another embodiment, expandable tissue retention device 450 may be partially or wholly opened to present a cone, elongated cone, or tapered dilator with a conical distal face, as shown in FIG. 6B. The dilator then assists in the device's passage through the body to the target site, e.g., by assisting in the passage through the hemostatic valve. In the event that a portion of the device is to act as a dilator, it is useful to have its distal portion covered, e.g., by a solid surface or by a mesh to ease passage. It would be preferably reduced to its lowest diameter at or before it reaches the RA for passage to the LA.

Bend 456 may be a thinner portion of strut 455, may be formed of different material, or may be otherwise biased outward, e.g., by a shape memory material such that it is nominally open, or pushed out by a lever (not shown) and is nominally closed absent the actuation. When tissue retention device 450 exits its sheath 50 or catheter 10 by being advanced on its shaft 457, it may automatically expand to a larger diameter (as shown in FIG. 6B) or it may expand upon actuation, e.g. with a pull wire. The tissue retention device 450 may have a shaft in its middle that pulls tip 470 toward shaft 457, forcing the expansion of the struts 455. The expansion may result in a variety of shapes. As shown, the shape may present a conical face to the tissue 30, tenting the tissue 30 into the lumen of the opposite tissue retention device 440. In the alternative, the tissue retention device 450 may be further opened and present a concave face to the tissue 30, providing all of the tissue retention force on the outside surface (and preferably at a similar diameter to that of cutter 416.

Tissue retention device 450 then works with a second tissue retention device 440 to trap the tissue. As described in detail above, tissue retention device 450 is advanced or retracted by its shaft 457 to be positioned alongside the tissue 30. Tissue retention device 440 is likewise advanced or retracted by its shaft 445 to be positioned alongside the opposite side of the tissue. In some embodiments the degree to which the tissue retention device 450 is opened is strictly controlled by preset activation. In others the physician can control the degree of opening, and thus the cut to be made.

In another embodiment the tissue retention device 450 is formed of a readily deformable material, such as stainless steel, or formed of a combination of materials, including a deformable material and a biasing material such as nitinol. In this embodiment it is delivered in its constricted or reduced form, as shown in FIG. 6A, and is nominally closed. That is, it is biased to be closed, or reduced to a smaller diameter, during delivery, as shown in FIG. 6A. At the desired location (e.g., in the LA if a distal tissue capture mechanism, or in the RA if a proximal tissue capture mechanism), it is actuated and deformed to an open or larger form as shown in FIG. 6B. Because the stainless can be deformed from one shape to another, once actuated the tissue retention device 450 is now nominally open. If any constraint is removed, it remains in the open position as a failsafe.

This design in general places high force point contacts on the tissue at the capture points. This design will likely be effective for a high force capture, especially when used in conjunction with a proximal capture device 440 designed like the one in 6B, with a raised perimeter edge. Ideally, if the struts are placed far apart, a thin filter is included to capture loose tissue.

After the tissue 30 is cut any distal element is deflated and it is retracted back into the catheter 10. Such a distal element may be deflated, collapsed, or otherwise reduced to fit within the catheter 10 (or other portion) either via actuation, or by being forced smaller as its withdrawn. Likewise, if the device utilizes a pigtail or discs they are withdrawn into or to the catheter after the tissue is cut. Likewise catheter 10 may utilize a suction device (not shown) to remove any tissue that is cut or loosened from the atrial septum. In one embodiment the tissue is then removed from the body while the catheter 10 is left in place. Accordingly, suction may be employed to remove the tissue through the lumen. Alternatively, the articulator may be on a separate catheter (not shown) contained inside catheter 10. This separate catheter may be withdrawn with the tissue. It may then be inspected to determine if the cut tissue was fully captured, cleaned and replaced, or replaced by a second, similar device, so that a second cut may be made safely.

Figure 2:
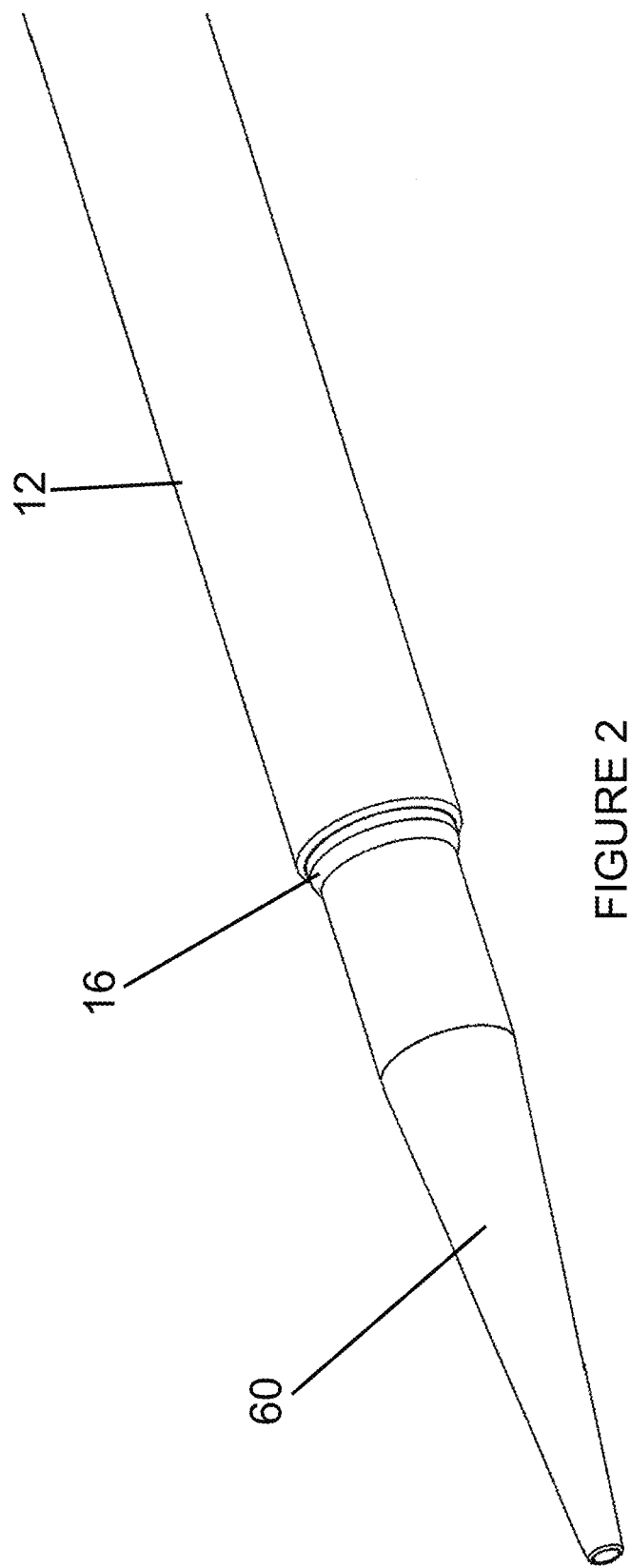
FIG. 2 is a partial perspective view of a catheter constructed according to the present disclosure.
Figure 2A:
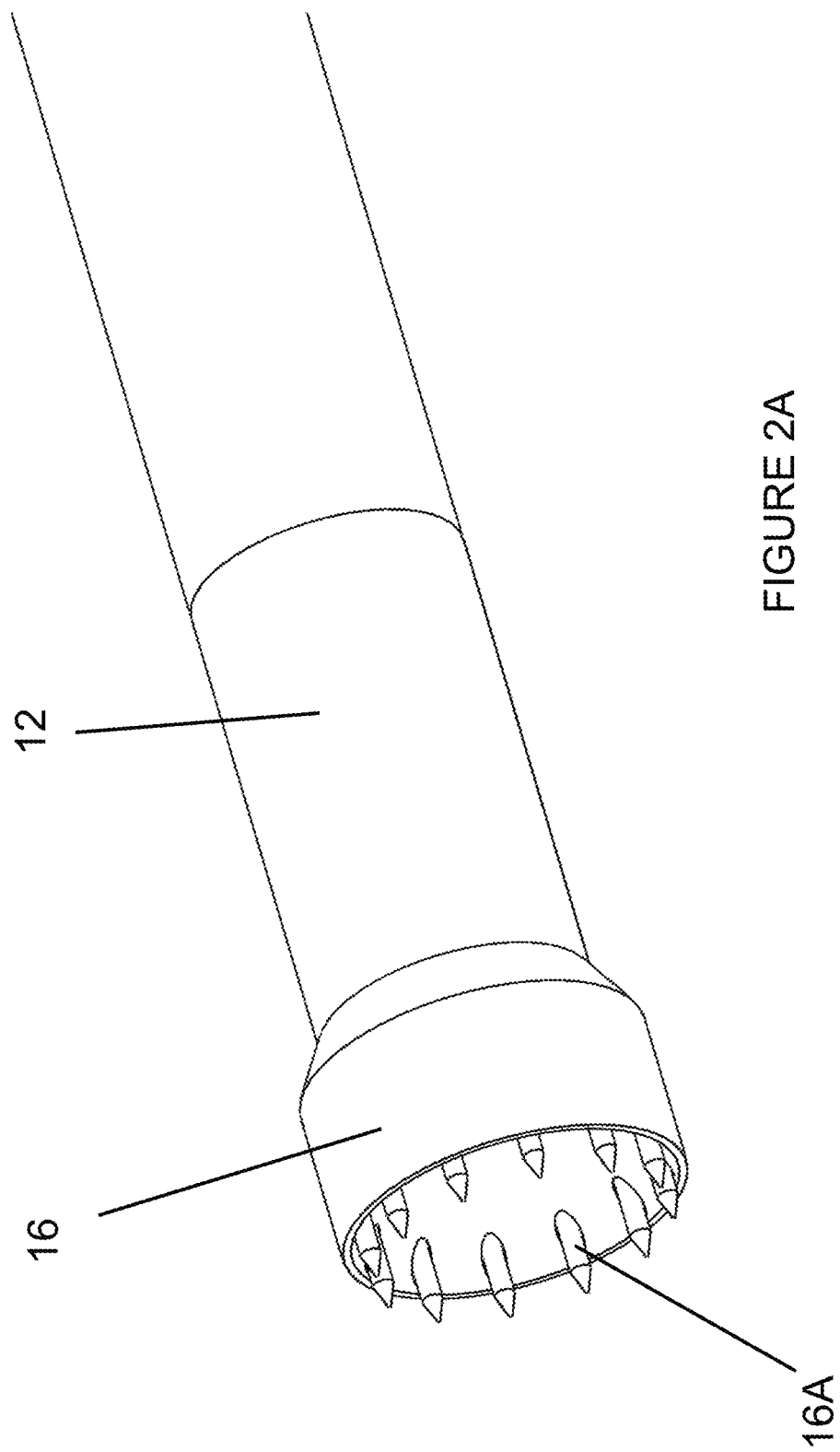
FIG. 2A is a partial perspective view of a catheter constructed according to the present disclosure.

The cutter 16 is preferably a shaped blade 16 located around the distal catheter lumen 32. In a first embodiment, shaped blade 16 is circular in shape and has on its distal end a razor like member formed of steel or another suitable metal or material. In a related embodiment the cutter 16 includes saw teeth 16A for cutting through the tissue 30. (See FIG. 2A). In another embodiment cutter 16 comprises rotary blade 16 and is capable of spinning or rotating to cut or form an incision. The rotary blade 16 may comprise a blade capable of spinning in relation to the catheter, or may comprise a distal cam action on the catheter shaft. Suction or another tissue holding mechanism is preferably employed with a rotating blade to hold the tissue in place while the cut is completed.

In other embodiments the cutter may be triangular in shape, square, or another polygonal shape such as an octagon, such that when forced through the tissue 30 the shaped blade 16 creates an aperture by cutting out an area of the tissue creating a hole, preferably a shaped hole. Notably, the shape of the hole may not match the blade precisely, e.g., an octagonal blade may create a circular hole, and tenting as described herein may substantially alter the shape of the hole, e.g., a circular blade may create an oblong aperture due to uneven tenting due to many factors, including inconsistent tissue elasticity or thickness. Likewise, the blade can provide an elongated slit with a small width and a radius on each end—to create a structure that has a small sectional area under low pressure, but increases in area with a high pressure differential.

Figure 1A:
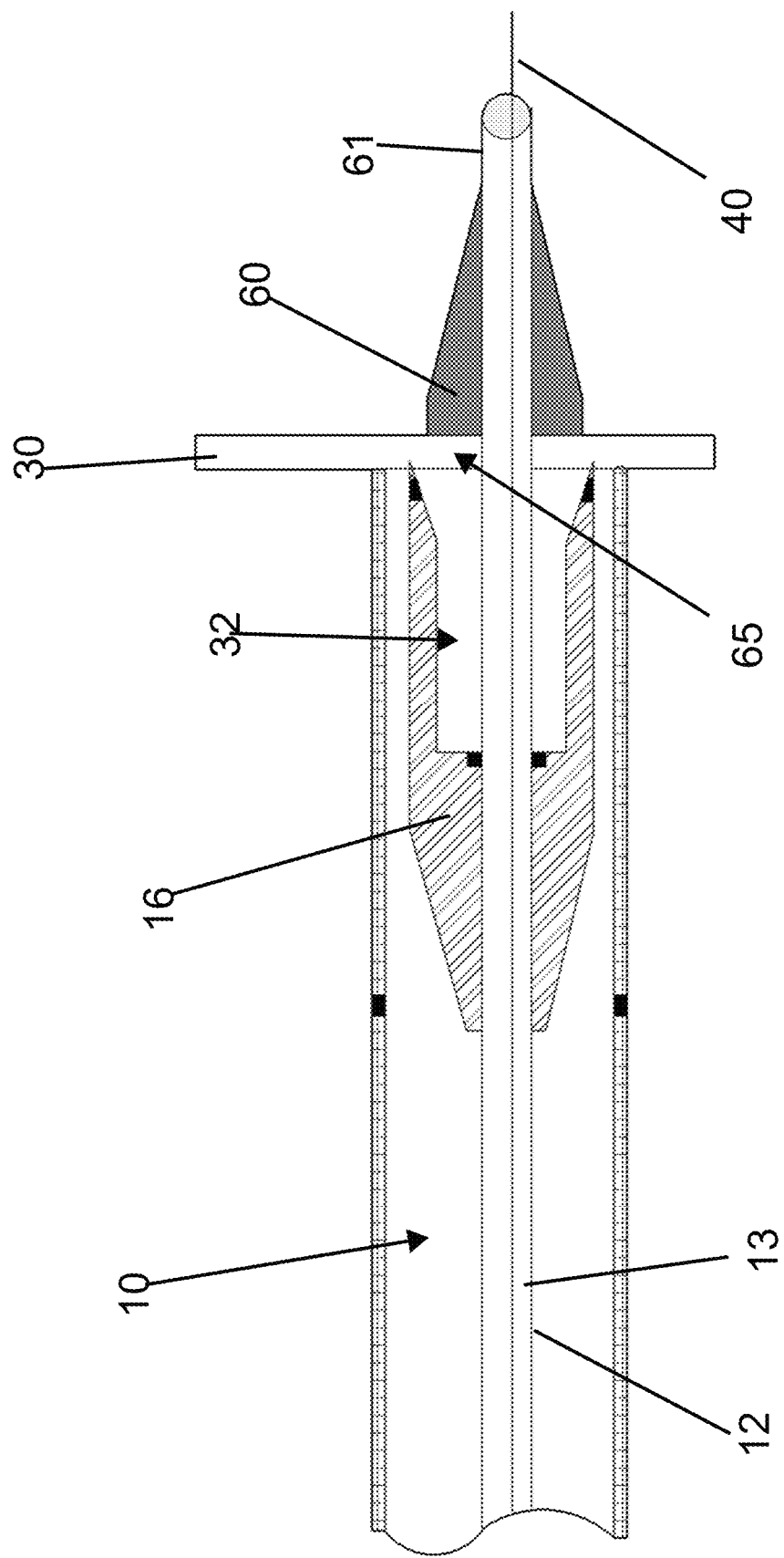
FIG. 1A is a partial perspective view of a catheter and a retention mechanism inserted into a target tissue.

As shown in FIG. 1A, in another embodiment catheter 10 includes shaft 12, lumen 13, distal lumen 32 cutting blade 16 as well as a tissue articulator 60, shown in a conical shape. Tissue articulator 60 is actuatable along the lumen 13. The tissue articulator 60 may be actuated for one of a couple purposes, including grabbing tissue, penetrating tissue, tenting tissue, with the cutting blade 16 cutting tissue, or retaining tissue. The tissue articulator 60 may be actuated multiple times for the same or different purposes. It may, for example, be actuated once to penetrate the septum 30. For any device that will penetrate the septum, it is helpful to have a tapered tip and a lubricious coating, to facilitate easy crossing. Likewise, to facilitate low force crossing of the septum it is important to have a low profile. Having a low profile also minimizes tissue tearing, which improves accuracy of shunt shape and size. It (or the blade 16) may then be actuated to retain the tissue, e.g., against the blade, and then actuated a third time for cutting.

The actuation may take one of several forms. An actuator on the handle may be used. Likewise, the tissue articulator 60 may ride on a guidewire or a catheter that is slidable relative to catheter 10 or cutting means 16. In such a case the actuator includes or actuates the catheter shaft and it may be slid back and forth as needed.

The tapered cone 60 in one embodiment is the tissue articulator 60, and is attached to a stainless steel tube 61 that comprises the outer diameter of lumen 13 or fits within lumen 13. The tapered cone 60 and the cutting blade 16 are both of a sufficient diameter to cut an aperture of the desired size. For example at its widest point the tapered cone 60 may be 6 mm wide. In operation the tapered cone 60 rides over a guidewire 40 that runs through a lumen 13 to the left atrium. The tapered cone 60 is forced through the atrial septum 30. As the tissue in the septum is elastic it will stretch over the tapered cone as it passes through and then will partially recover to fit in the space 65 between the tapered cone 60 and the cutting blade 16. The tissue may also have some tearing present. While the space 65 may be a longer space, which may allow for more tissue to be gathered into lumen 32, in one embodiment space 65 is a short narrow segment that only leaves enough of a longitudinal gap for the tissue 30 to fit between the distal tip of the cutting blade 16 and the cone 60, e.g., 2 mm. The tapered cone 60 is then actuated and pulled proximally into the lumen 32. Because the tapered cone 60 fits precisely within the lumen 32 it pulls into the lumen even if the catheter is at an angle or is bent. This action pulls the tissue 30 into the cutting blade 16, cutting an aperture in the interatrial septum. The tissue 30 is captured within the lumen 32 and held in place by the withdrawn tapered cone 60 and removed from the body. Of course, the cutting blade 16 may be actuated forward or into cone 60 to cut the tissue.

The tapered cone 60 may have a drug coating for one or more purposes. For example, it may have a hydrophilic coating to reduce tearing as it passes through the interatrial septum 30. A slippery tapered cone 60 will reduce tenting due to friction as it passes through the tissue. Likewise the tapered cone 60 may have a drug coating that will slow fibroblast proliferation and migration as well as the secretion of extracellular matrices, e.g. Pacelitaxel. Likewise, the cutting blade 16 may include one or more of these coatings.

Figure 3:
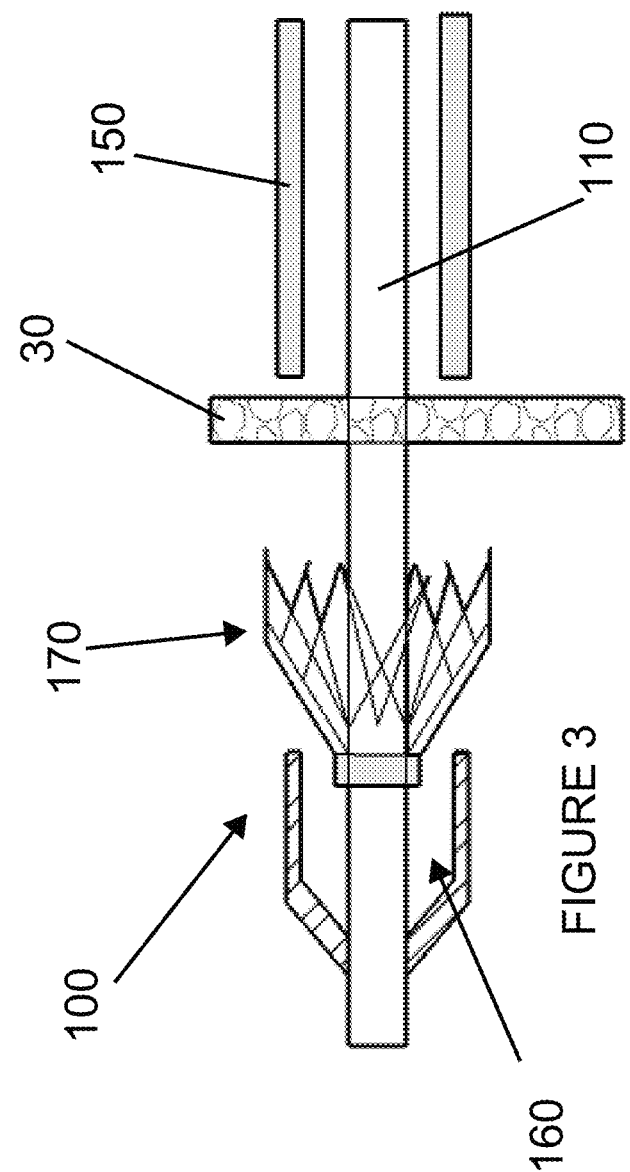
FIG. 3 is a partial perspective view of a catheter constructed according to the present disclosure.

Cutter 16 can take a variety of forms. In another embodiment, as shown in FIG. 3, the cutter is formed into a basket of a shape memory metal or a nitinol basket, so that when it is fully retracted and inside catheter 10 it takes a more linear shape or a compact shape. However, when the cutter exits the catheter it assumes one of a number shape of shapes, such as a loop or basket, as disclosed in U.S. patent application Ser. No. 15/089,547, filed Apr. 2, 2016, and incorporated herein by reference. Alternatively, the cutter may comprise blades, retractable or otherwise, on the side of the catheter 10 to create a patterned cut, as disclosed in the '547 application. Of course, the cutter may be a combination of one portion that creates a hole, and a second that creates a separate hole or patterned cuts. Likewise, multiple cutters may be used. For example, a first cutter may approach the tissue from the distal side and a second cutter from the proximal side, cutting with a scissors action. In addition a cutting device may comprise a semicircular blade. The semicircular blade may be rotated such that as it is rotated it will create a circular hole in the tissue. The cutting device may take alternative forms. Similar to the semicircular blade, the blade may take the form of a coiled blade (not shown). The coiled blade may be contained within the lumen of the catheter. Once deployed out of the catheter and uncoiled the blade is used to cut a hole in the septum as above. The coil may take several forms. For instance the coiled blade may take the form of an auger (not shown). Likewise the coiled blade may take the form of a coiled rolled sheet that expands the farther out of the lumen it is pushed. Both such forms may give the physician discretion as to how large of an aperture he wishes to create in the interatrial septum.

With reference to FIG. 3, in a further embodiment the catheter 100 includes an expandable cutter 170. The cutter 170 may formed of nitinol or stainless steel, and may be nominally open or nominally closed. In use, the catheter 100 is inserted into the right atrium while inside sheath 150. Sheath 150 protects the surrounding vein and other tissue from the cutter 170 until the catheter 100 is in place to create the aperture. There are two broad mechanisms of action. First when catheter 100 is placed against the interatrial septum tissue 30 the introducer 150 may be actuated and withdrawn allowing cutter 170 to open. At this point the catheter 100 is actuated or pushed through the interatrial septum 30 and the cutter 170 creates a cut or a patterned cut in the tissue. In the case of a shaped cutter or basket the cut may be circular or otherwise shaped. In the case of four blades the pattern cut appears as an X. The four flaps of tissue that are created will provide a durable aperture.

The physician may also push the introducer 150 up against the interatrial septum 30, as shown in FIG. 3. The catheter 100 with the cutter 170 still retracted may be pushed through the interatrial septum 30. As or after it passes through the septum, the catheter 100 exits the introducer 150, or a cutter sheath (not shown) that is located directly around the cutter 170, allowing the cutter 170 to deploy. The catheter 100 is then pulled back in a proximal direction towards the right atrium cutting the tissue in the desired pattern. As the catheter 100 is pulled back in the proximal direction and after it has created the desired cut it will reenter the sheath 150 or the cutter sheath retracting the blades for removal from the body.

With reference to FIG. 3, the cutter 170 may be extended by any combination of a biasing arm, pivots, springs (not shown) or biasing materials such as nitinol. In such a case the cutter will typically automatically extend when there are no restrictions on it, e.g., as the catheter exits the catheter sheath or after the catheter has pushed through the interatrial septum to the left atrium, the cutter is nominally open. In addition it may be advantageous to have the cutter automatically fold in based on contact from one direction and automatically extend when that contact is removed. Thus for example the blades may extend based on contact from a distal side e.g. as the catheter pushes into the interatrial septum the contact with the tissue pushes a cutter in the proximal direction, causing the cutter to open out from the catheter shaft 110. The cutter may then automatically withdraw back into the catheter as the catheter is pulled back through the interatrial septum and the catheter blades are contacted from the proximal side by the tissue or a sheath, or vice versa. Likewise, a combination of biasing or contact may alternately open or close the blades. For example the cutter may be biased to open if there are no restrictions, but may be closed using contact with the tissue, sheath, or introducer as it is withdrawn. Likewise the cutter 170 may be extended via an actuator on a handle. It can be desirable to employ suction through a lumen in the catheter 100 such that any tissue dislodged during the cutting process is safely removed.

In one embodiment, catheter 100 is pushed through the interatrial septum 30 to the distal side. Catheter 100 includes a lumen 160. Lumen 160 is closed in the distal direction as shown, but is open in the proximal direction. Nestled within lumen 160 is a nitinol basket. Upon actuation the nitinol basket 170 is withdrawn proximally or the lumen is advanced distally. In a first embodiment, as the nitinol basket 170 exits the lumen 160 it expands substantially forming a much wider basket. The proximal points and edges of the basket are sharp and accordingly may be drawn into and through the tissue both cutting the tissue to create the aperture, and retaining the tissue for removal. After the aperture is created, the catheter is actuated a second time and the nitinol cutter 170 is pushed or pulled back into the lumen 160 or otherwise activated to cause it to close back up for removal from the body. In embodiments, the cutter may operate with one or more tissue retention devices. For example, the cutter may ride over a proximal tissue retention device such as the one pictured in FIG. 4 (256), 5B (340), 6A (440), or 9A (740) below. Likewise, the cutter may operate with or ride over a distal tissue retention device, such as balloon 42, a pigtail, a basket 355, a cone 450 or a disk 750. In another embodiment, the cutter 170 acts as a proximal tissue retention device and a basket 355 or cone 450 operates as a proximal tissue retention device.

In a second embodiment, as the nitinol basket 170 exits the lumen 160 it expands substantially forming a much wider basket to serve as a tissue retention device to retain the tissue or to hold the tissue into a cutting means. As depicted, the proximal edges of the basket may be sharp and accordingly may be drawn into the tissue to hold it and bias it into the cutting means (not shown). The basket 170 may also lack sharp edges and may simply bias or retain the tissue, for example forming a spherical basket 170. After the aperture is created, the catheter is actuated a second time and the nitinol basket 170 is pushed back into the lumen 160 causing it to close back up for removal from the body.

Figure 4:
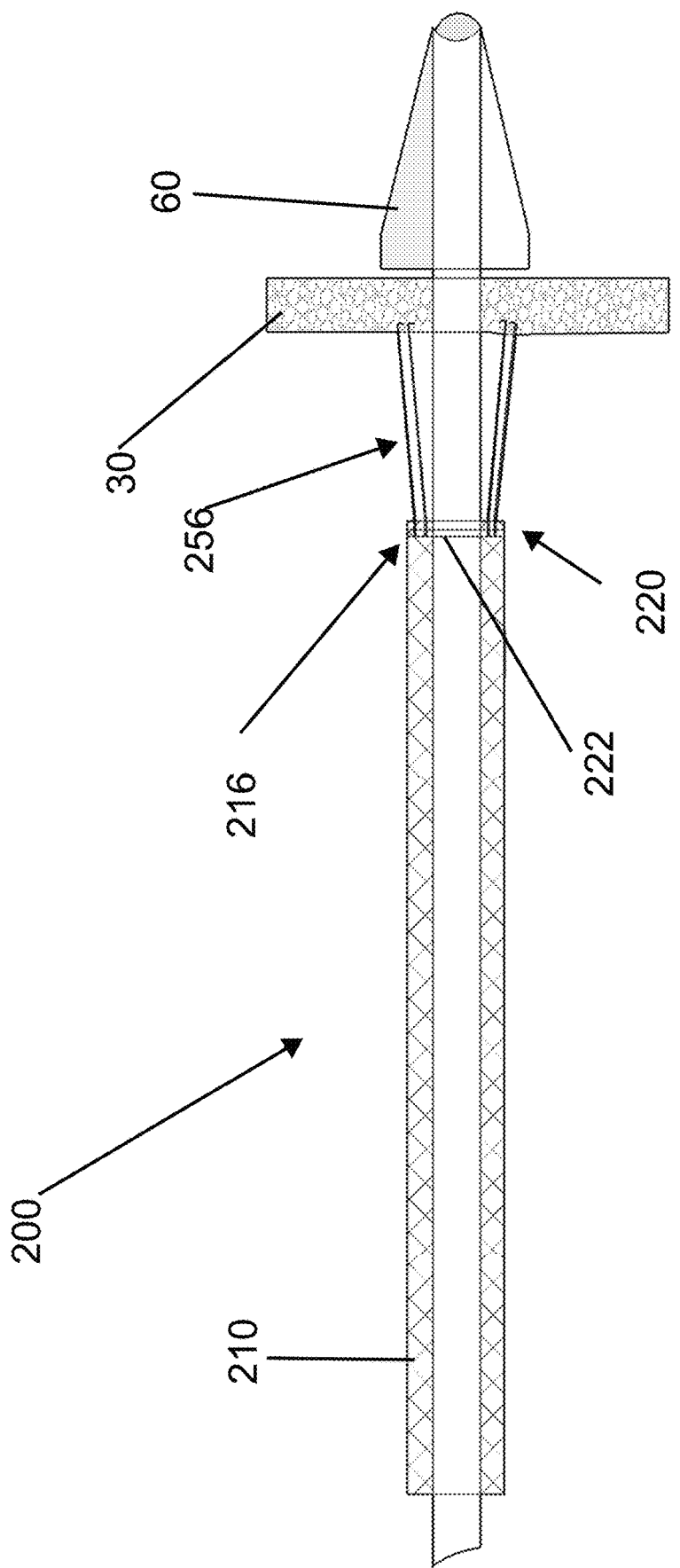
FIG. 4 is a partial perspective view of a catheter constructed according to the present disclosure.

Referring to FIG. 4, in another embodiment of the catheter 200, the catheter 200 comprises an elongated hollow catheter shaft 210 having an interior lumen in which one or more hooks 256 are positioned. The catheter 200 further comprises a distal end 220 with a lumen 222. The hooks 256 are extended out of the catheter shaft 210 and lumen 222 and into the tissue of the interatrial septum 30. Once the hooks 256 firmly grasp the tissue, the hooks 256 are drawn back into lumen 222 to positively retain the tissue 30. While four hooks are shown in FIG. 4, the number of hooks may vary and in particular embodiments with one hook to four hooks are contemplated.

As shown in FIG. 4, when the tissue 30 is grasped by hooks 256. In one embodiment hooks 256 merely hold tissue 30. In another, tissue 30 is withdrawn into the lumen 222 the cutting device 216 may be employed to cut the aperture into the tented tissue 30. FIG. 4 depicts the hooks 256 as orienting towards the center of the catheter's central axis. However it is also contemplated that the hooks may be oriented away from the axis of the catheter in another embodiment. Likewise hooks 256 are shown as a long thin rod with a short hook on the end. However, in another embodiment the two hooks more resemble the long grasping arms of a sturdy pliers.

Tissue 30 may be grasped by hooks 256. Preferably hooks 256 are designed to grasp the tissue 30 such that the blade 16 will ride over them to cut the tissue just outside of where the hooks grasp the tissue. As shown in FIG. 4, tissue articulator 60 may serve as a distal tissue retention mechanism, and as such the cut tissue is held between the tissue articulator 60 and hooks 256, and withdrawn into the lumen of cutting device 216. Alternatively, tissue 30 may be grasped by one or more corkscrew elements (not shown), adhesive, a barbed insert, suction, or the like. Of course, a combination of grasping mechanisms may be effective.

Figure 9A:
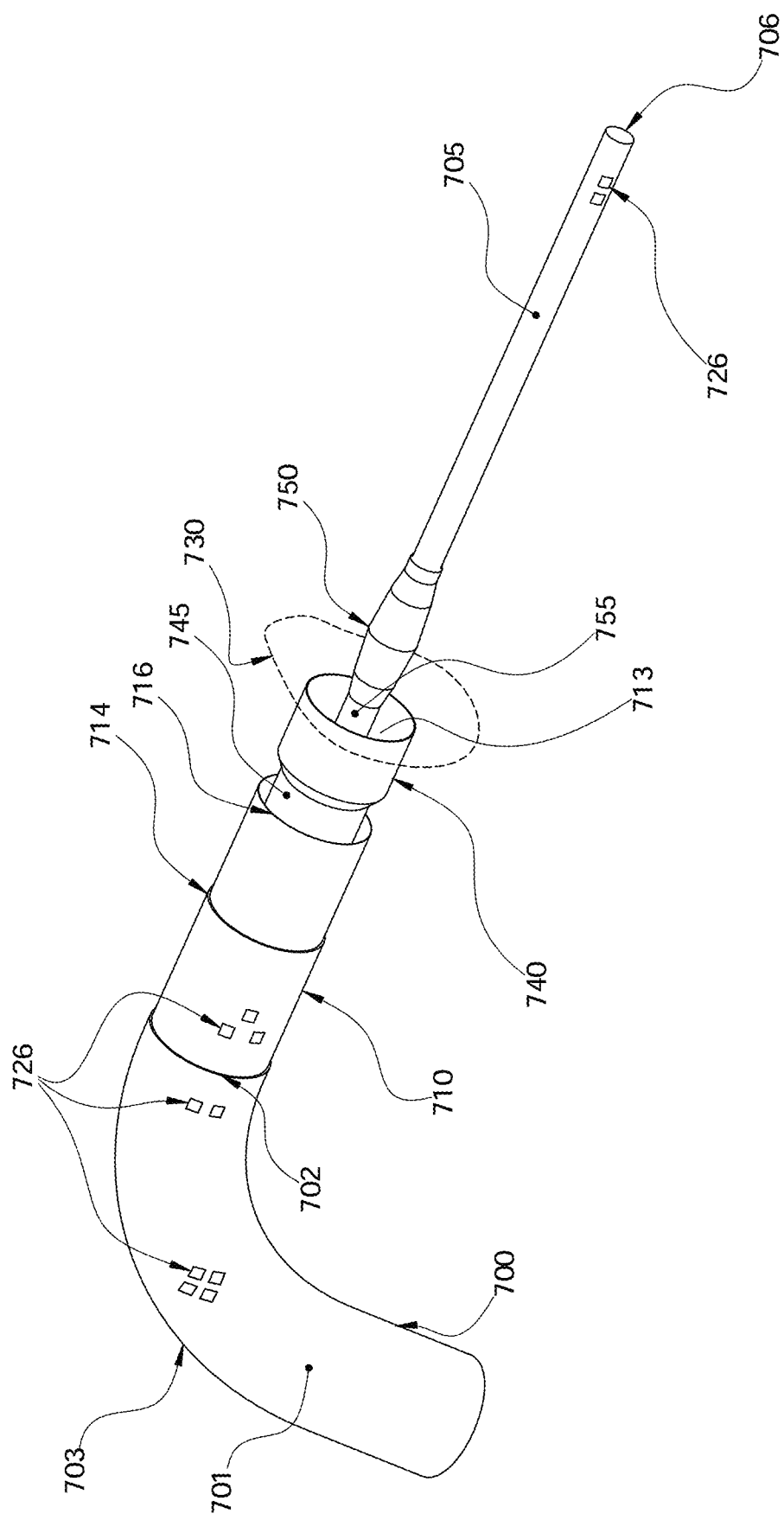
FIG. 9A is a partial perspective view of a catheter constructed according to the present disclosure.
Figure 9B:
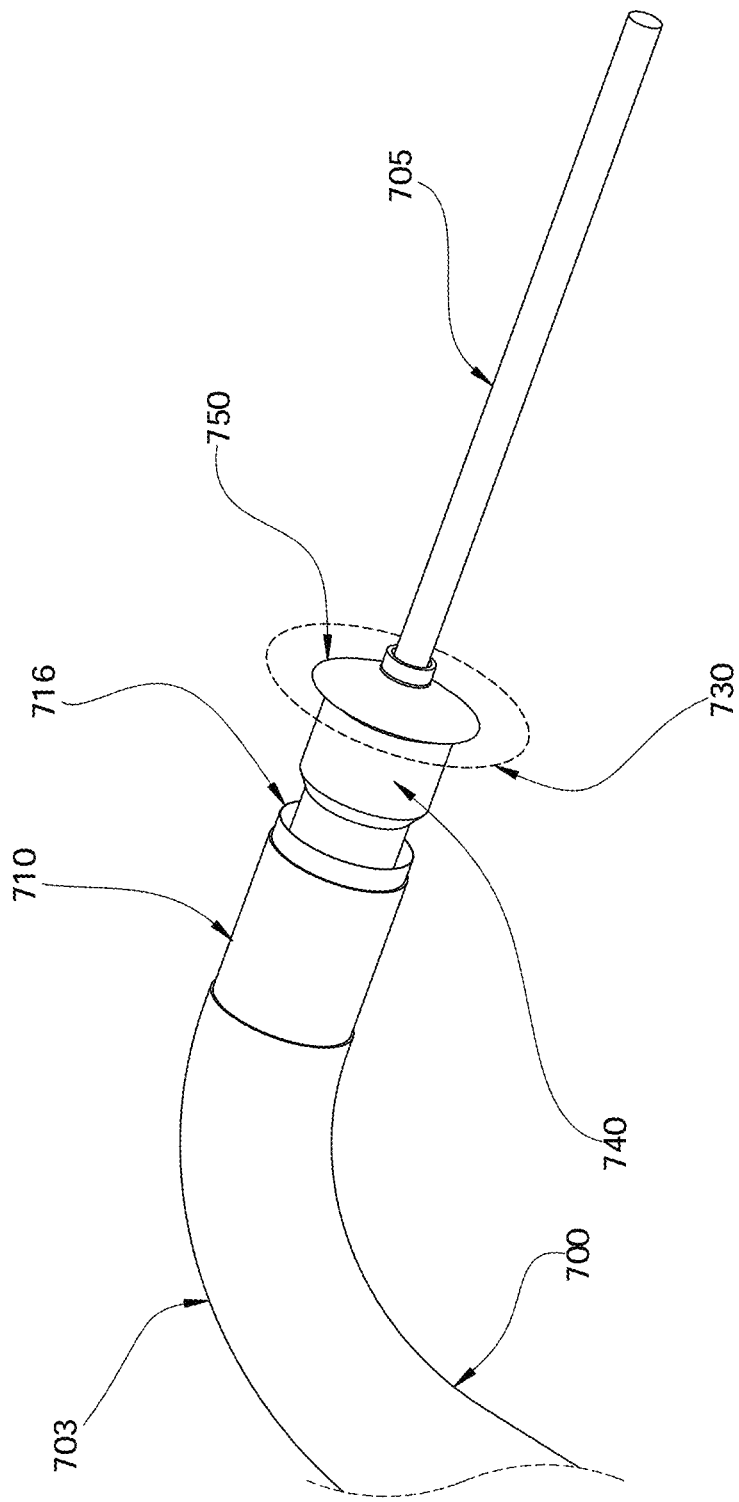
FIG. 9B is a partial perspective view of a catheter constructed according to the present disclosure.
Figure 9C:
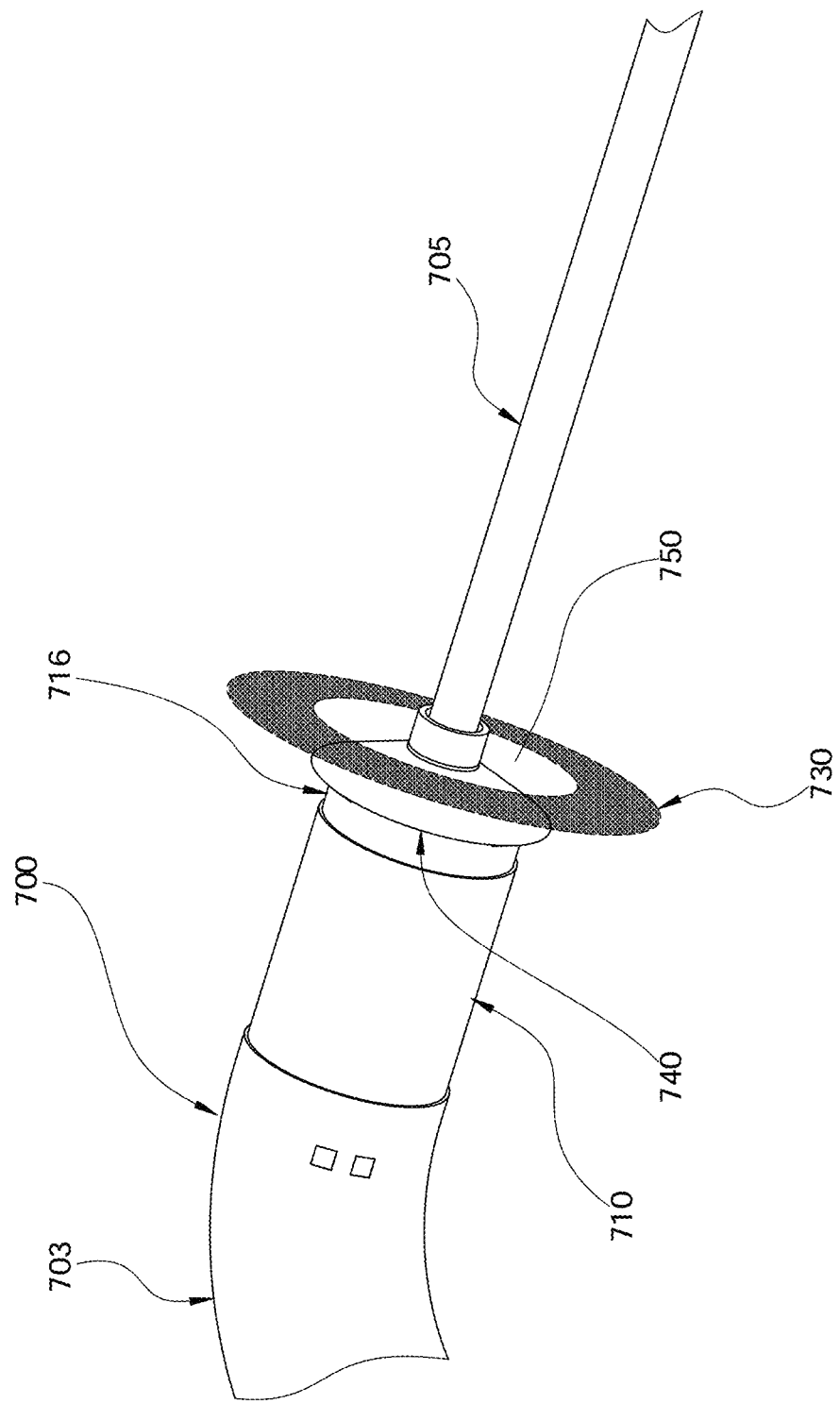
FIG. 9C is a partial perspective view of a catheter constructed according to the present disclosure.

With reference to FIGS. 9A-C, a medical device assembly includes a sheath 700, a catheter 710, and a guidewire 705. While the following description describes the sheath 700, catheter 710 and guidewire 705 as separate devices, it is understood that they equally can be a single device, be integrally connected (but preferably laterally moveable relative to each other), and be controlled by the same or different proximal handles and electrical connections. In particular, the attributes of the sheath 700 and catheter 710 may be advantageously combined. Likewise, the sheath, catheter, or guidewire may be omitted. While at least one of the devices will need to traverse the length of the body from the entry point to the atrium, it is contemplated that the other devices may be shorter. For example, the sheath may traverse from the percutaneous entry point to the right atrium. The catheter may only traverse from one side of the right atrium to the other, for example, and as such be substantially shorter.

Sheath 700 comprises an elongated catheter shaft 701 having a distal end 702 and a proximal end (not shown). The proximal end includes a handle (not shown). The handle may comprise actuators, such as a first actuator, a second actuator, and a third actuator (not shown). It is understood that in the case of multiple handle units on different portions of the assembly, any one of the actuators discussed in the following may be on different handles connected to any of the three components (sheath, catheter, guidewire). The handle(s) may further include fluid port(s) and electrical connection(s) (not shown). Sheath 700 and/or catheter 710 may further include pull wires attached to an actuator for actuating distal elements, moving a lumen or shaft, steering, or the like. Sheath 700 and/or catheter 710 may further include irrigation ports and the like.

Sheath 700 and/or catheter 710 further include visualization markers 726 designed to allow the physician to determine the location and orientation of the sheath 700 and catheter 710 in the patient and the orientation of the different components of the device relatively to each other. For instance, sheath 700 may have radiopaque markers 726 at a bend 703 in a pattern that identifies the bend region. Sheath 700 may then have further radiopaque markers 726 at its distal end 702, again in a distinct pattern that is the same or different from the pattern at bend 703. Likewise catheter 710 may have radiopaque markers 726 at its distal end. Because the catheter 710's radiopaque markers are differently patterned than the sheath 700's radiopaque markers, the physician will be able to quickly and easily identify when the catheter 710 exits the sheath 700. Finally, guidewire 705 may have radiopaque markers 726 so that the guidewire may be quickly identified by fluoroscopy as well. Preferably, the radiopaque markers 726 (or other markers) on the catheter, sheath and guidewire are distinguishable from each other and accordingly the physician is able to determine the spatial relationship of the three components. In one example, spot electrodes may be used and provide a pattern. In another example, an electroanatomical mapping system is programmed or provided with the specifics of the three components. The specific electrodes, magnetic coils, or other electrodes are identified to the mapping system, e.g., through an EEPROM in the catheter or otherwise, and as the system identifies a specific electrode or coil (e.g., by the current passed through the electrode or coil and to the other components of the mapping system). The mapping system may then clearly and visually identify the location of the three components for the physician.

Advantageously, the sensors may enable the operator to create an electro anatomical map of the right atrium and left atrium. This map can include details such as tissue thickness, especially in the fossa ovalis or the septum. The maps can also be created or supplemented by fluoroscopy, or an imported map such as a CT scan, MRI, live external modalities like TTE, TEE, or information from live on-board catheter sensors, like OCT, ultrasound, CCD camera visuals, for example, to understand the surface morphology, tissue thicknesses, tissue compliance, location of PFO/flap, etc. These live modalities maybe also used independently. For example, the live on-board catheter sensor(s) may be an OCR sensor for imaging the tissue to be cut. This design might also incorporate a live on-board catheter sensor, which is an electrode to keep cutting away from nerve, SA node artery, or for impedance tissue thickness measurements, as examples.

Sheath 700, guidewire 705 and catheter 710 may alternatively or further include ultrasound markers (not shown) or hyper-echogenic markers, again preferably in designed patterns as described above such that the physician may locate the components in the patient on ultrasound imaging. In an alternative embodiment, in place or in addition to radiopaque markers 726, the sheath 700, guidewire 705, and catheter 710 may have electrodes (not shown) that are locatable on an electroanatomical mapping system such as the EnSite™ electroanatomical mapping system. Alternatively, the sheath 700, guidewire 705, and catheter 710 may have magnetic coils locatable on the Carto™ or Medi-Guide™ mapping systems.

The elongated shaft 701 is preferably hollow, having a lumen 713 that has the ability to pass the catheter 710 and guidewire 705 through it. The catheter 710 is designed to work in conjunction with sheath 700. Sheath 700 may either extend the entire length from the percutaneous incision to the left atrium of the heart, or may only cover a portion of catheter 710.

To achieve a consistent aperture of the shape desired by the physician, it is desirable that the cutting blade enter the tissue 730 perpendicularly to the tissue 730. Unlike that taught in the prior art devices, where the angle of tissue approach is not addressed, the inventors herein have found that the more squarely the cutting blade 716 addresses the tissue 730, the more predictable the size of the aperture and the quality of the aperture. Accordingly, the sheath 700 and the catheter 710 are designed to provide the operator with the ability to provide a right angle approach to the tissue. In another embodiment, the distal plane of the cutter is orthogonal to the plane of the tissue being cut. That is, the entire face of the cutting blade cuts the face of the tissue substantially simultaneously. Because of tissue irregularity it is noted that the blade does not exactly contact the tissue simultaneously. Likewise, the blade may be a saw-toothed or Franseen blade, and may not be capable of a perfectly simultaneous cut, but rather a substantially simultaneous cut where each section of the blade cuts at the same time.

The ideal location for creating the aperture is across the thinnest tissue of the fossa, because it is the easiest to cut. However, if the fossa is crossed without controlling the angle of the crossing the circular blade may cut a hole that is not circular and not the expected size. Also, a shallow angle can lead to the cutter inadvertently cutting unintended tissues, like the atrial wall, causing a safety issue. Finally, after a device, such as a guidewire or catheter crosses the septum, and the angle, side force, or side bias is not controlled by adjusting the angle of the device, the device can inadvertently tear or stretch the tissue. If the tear or stretch is significant enough it will impact the resulting shape of the aperture, and in the worst case the tear will stretch into the location of the cut such that the blade is not cutting any tissue in the location of the tear or the tissue is not retained.

In one such embodiment, sheath 700 extends to the steering/bend 703. In another embodiment the sheath 700 may terminate before the bend 703, and as such the medical assembly is preferably steered/bent by pull wires or biasing in catheter 710. However, in another embodiment, the sheath 700 terminates distally of bend 703. Pull wires or biasing in the sheath 700 enable it to make a sufficient turn to orient catheter 710 toward the interatrial septum 730 and thus the sheath exit and orientation provide an orthogonal guide to the catheter. If the sheath is then locked in place, e.g., via a catheter hub (FIGS. 7, 8) its bend 703 can operate to prevent catheter 710 from moving upward in the RA. While in one embodiment the catheter 710 does not have its own biasing or pull wires, in another embodiment the catheter 710 may be separately steerable or biased, and thus provide for the orthogonal approach. Pull wires provide the advantage of minute adjustments to the specific anatomy of the patient, and allow for greater flexibility in the device. One device may be used for nearly all patients and still provide a proper approach angle.

In another embodiment the catheter is controlled by steering the distal magnetic field. Remote magnetic navigation operates by, for example, using two large magnets placed on either side of the patient, and alterations in the magnetic field produced by the magnets deflects the tips of catheters within the patient to the desired direction. The physician operates the catheter with screen a joystick. The catheter itself is advanced by the joystick, instead of the physician's hands. Likewise, while a physician may operate the medical devices disclosed herein by hand, the devices may be robotically driven. As with magnetic navigation, the physician operates the catheter with a screen and a joystick. In another embodiment, providing a biasing agent such as a nitinol wire to provide a preformed bend provides the advantage of having a less expensive manufacturing process and a simpler device. However, multiple bend sizes may need to be manufactured.

In another embodiment, the sheath 700 may have a first preformed bend, and the catheter 710 may have a second preformed bend. The first and second preformed bends work together to allow the operator to direct the cutting blade 716 to the septum at a right angle. Likewise, the catheter 710 may have multiple preformed bends. For example, a catheter 710 may have a first and second catheter preformed bend, such that for a smaller atrium only the first bend exits the sheath 700, and with the sheath's orientation, the first bend directs the distal end of the catheter to where the fossa ovalis typically sits for a small heart with smaller chambers. For a larger heart, however, as the catheter 710 must exit farther out of the sheath 700 the second catheter bend also exits, and realigns the distal end of the catheter toward where the fossa ovalis typically sits for a larger heart. Likewise, the assembly may include a removable stiffener that can be deployed to adjust the distal tip's location to provide a right angle approach to tissue 730.

The sheath 700 and the catheter 710 may include braiding to provide stiffening. Unlike prior art devices which create a hole by energy sources or by implanting a device, the present device may find that significant pressure is necessary to create the aperture. Because the pressure must be transmitted from the length of the sheath or catheter that pressure will initially push the cutting edge and the entire catheter along rather than through the septum. For example, in a femoral vein entry procedure, the catheter is initially pushed upwards in the RA rather than towards the left atrium. Accordingly, unlike the prior art the applicants have discovered that providing stability and steerability in either the sheath or the catheter may greatly reduce this upward pressure and redirect the force towards the interatrial septum 730 to provide a proper cut. In particular bend 703 and the adjacent shaft may require a stiffer shaft than the remainder of sheath 700.

Toward this end, sheath 700 is used to create bend 703 and direct the catheter 710 to the septum 730. Sheath 700 terminates just distally of the bend 703. At this point, in one embodiment the sheath 700 is held in place as catheter 710 is advanced out of the sheath 700 to the septum 730. Because the sheath 700 is sufficiently stiff, it resists the upward pressure and directs the catheter force toward the interatrial septum 730. Together or in place of the sheath, the device contemplates providing anchoring means or stabilizing means (not shown) to prevent the catheter and the cutting blade from shifting and thus allowing a clean cut in the desired location. Sheath 700 and catheter 710 may further include irrigation ports (not shown).

The distal end 714 of catheter 710 comprises a cutting means 716. In a first embodiment the cutting means 716 is a razor like member formed of steel or another suitable metal or material adapted to cut a thin tissue. Toward this end the cutting means may be very thin so that it cleanly and easily pierces the thin tissue. In those embodiments where cutting means 716 has a sharp edge at the end of the catheter 710, it is preferred that the sheath 700, catheter 710, proximal capture component 740, or distal capture component 750 cover and protect the vein and other tissue from the cutting means 716 until the catheter 710 is delivered in place and actuated by the physician to cut the target tissue. In a preferred embodiment, the cutting means 716 has its sharp edge on its ID, and rides flush with or just over proximal capture component 740, thus protecting the tissue from the blade. In other embodiments a cone (not pictured) or other distal element may cover or sit flush with the cutting blade 716 so that the blade is protected until actuation. The cutting means may be actuated by the advancement of a cutting means shaft (not shown) that sits within a lumen of catheter 710. It may also be advanced by action of a pull wire, or via a twisting action driving a screw attached to the blade forward.

The cutter 716 in one embodiment is a shaped blade 716 located around the distal catheter lumen 713. In a first embodiment, shown in FIG. 9A, shaped blade 716 is circular in shape and has on its distal end a razor like member formed of steel or another suitable metal or material. In a related embodiment the cutter 716 includes saw teeth for cutting through the tissue 730. In another embodiment cutter 716 comprises rotary blade 716 and is capable of spinning or rotating to cut or form an incision. For example, if the blade is driven forward via a rotary action, that rotary action may be accomplished by the screw mechanism above. The rotary blade 716 may comprise a blade capable of spinning in relation to the catheter, or may comprise a distal cam action on the catheter shaft. An actuator on the handle may generate the rotation. Suction or another tissue holding mechanism is preferably employed with a rotating blade to hold the tissue in place while the cut is completed.

In other embodiments the cutter may be triangular in shape, square, or another polygonal shape such as an octagon, such that when forced through the tissue 730 the shaped blade 716 creates an aperture by cutting out an area of the tissue creating a hole, preferably a shaped hole. Notably, the shape of the hole may not match the blade precisely, e.g., an octagonal blade may create a circular hole, and tenting as described herein may substantially alter the shape of the hole, e.g., a circular blade may create an oblong aperture due to uneven tenting due to many factors, including inconsistent tissue elasticity or thickness.

Figure 10B:
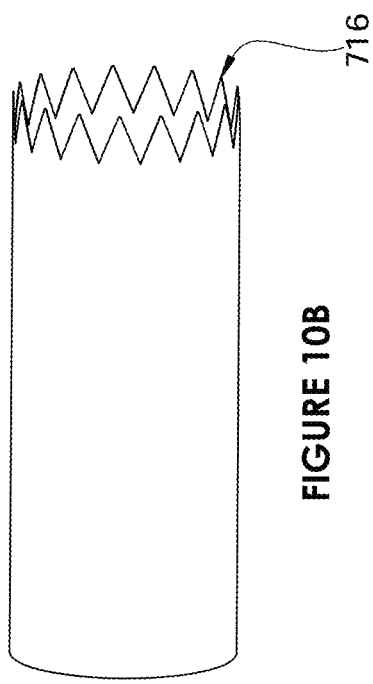
FIG. 10B is a partial perspective view of a cutter constructed according to the present disclosure.
Figure 10A:
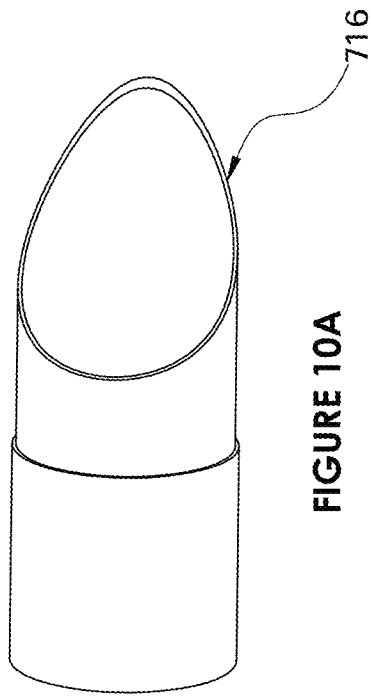
FIG. 10A is a partial perspective view of a cutter constructed according to the present disclosure.

As shown in FIG. 10A, cutting blade 716 may be an angled hypodermic blade. The cutting blade may have a lancet point. As only a portion cuts at any one moment, the pressure required to create the aperture is greatly reduced. As shown in FIG. 10B, cutting blade 716 may be a saw blade (pictured) or may also be a Franseen blade. As shown in FIGS. 10A and 10B, such blades may have a hollow lumen. When employed to cut the aperture, the lumen may be placed under a vacuum to remove any and all debris removed from the tissue 730. The cutting means 716 may be a serrated blade which will allow for a lower cutting force. Likewise the cutting means 716 may comprise a vibrating or impulse blade to likewise allow for a lower cutting force.

Regardless of the tissue removal or retention means, it is advantageous to include a tissue collection device. For example, the catheter may include a lumen or compartment at the distal end to retain the tissue. Likewise, under suction the device may include a tissue trap, such that fluid, blood, or other material may pass, but tissue is retained in the trap. The physician then may monitor the trap to determine that the tissue removed from the septum has been captured, and is not still in the heart. Such a monitoring may be automatically provided, or may be manual by the physician. It is advantageous if such monitoring can be conducted before the catheter is removed from the patient, and as such in one embodiment the trap is exterior to the body and readily accessible by the physician. In another embodiment, the trap is automatically monitored by a sensor, such as an electrode, visual examination, pressure sensor, or the like for the presence and volume of tissue. In another embodiment the trap is removed for examination first, before the introducer and catheter are removed.

Additional cutting means can include a harmonic scalpel, an RF cutter, a high pressure fluid jet, or a laser. The devices can cut by rotation, a high density ring of points, or a low density ring of point that causes perforation in the tissue that can later be separated.

In one embodiment, shown in FIG. 9A the guidewire 705 is first positioned across the septum 730. Guidewire 705 can pierce the septum itself using a sharp tip 706 to cut a small hole in septum 730. Alternatively a separate device, such as a BRK needle (not shown), may be used to pierce the septum. Guidewire 705 may ride over or inside the needle to cross through septum 730.

In one embodiment, once the sheath is in place a transeptal crossing system is used to cross the fossa. Then once across, the crossing system is typically replaced with a guidewire. The guidewire 705 remains in position across the interatrial septum and guides either the sheath 700, the catheter 710, or both into position. Guidewire 705 may comprise a retention means on its distal end. Likewise, a guidewire may be positioned across the septum and a second catheter 705 may have a retention means 750. Catheter 705 may follow the guidewire through the septum. In an alternative embodiment, the transeptal crossing system is entirely separate and can cross the septum and position the guidewire before sheath 700 is inserted into the body.

Riding over the top of guidewire 705, the cutting means 716 is positioned next to or near the interatrial septum. The cutting means 716 may be so located through a physician's experience touch and feel, or using the markers, or in conjunction with imaging system.

Once the cutting means 716 or the catheter 710 are located next to or near the target tissue 730 the catheter 710 and/or the cutting means 716 are advanced past the end of or to the end of the sheath and placed in contact with the tissue 730. Preferably using the unique markers the physician can tell on the visualization system when the catheter has exited the sheath 700 or has contacted the tissue. Likewise, the catheter 710 or the cutting means 716 may include sensors (not shown) that identify when it contacts the tissue, at what angle it contacts the tissue, the thickness of the tissue, whether it is through or not through a PFO or a flap, if the cutting is complete, the quality of the cut edge, and the like. Such sensors can include a force sensor, fiber optics, a camera, and electrode using impedance sensing, mapping systems, ultrasound, or the like. Likewise, the physician may monitor a visualization system to determine when the tissue begins to tent to determine when contact is made. In a first embodiment, the circular cutter 716 is advanced into the tissue 730 to cut a circular aperture in the tissue. In an alternative embodiment the sheath 700 is not utilized and the catheter 710 itself is steered into position near tissue 730, and the cutting means 716 is advanced to cut the aperture.

It is preferred that one of the first, second, or third actuators be utilized to advance the catheter 710 out of the sheath 700. It is likewise preferred that an actuator be utilized to advance cutting means 716 out of catheter 710. However, either can be manually advanced without an actuator as well.

In another embodiment the medical device assembly includes a tissue capture component. For example, as shown in FIG. 9A, the assembly may include a distal capture component 750 designed to cross the septum to the distal side. The distal capture component may be attached to the guidewire or second catheter 705, the sheath 700, or the catheter 710. It may also be attached to a distal capture catheter 755. As such, distal capture catheter 755 may have a lumen and ride over the guidewire 705, but inside a lumen of catheter 710. Such a lumen may be just large enough to fit over a 0.035" guidewire. Distal capture catheter 755 may be advanced by an actuator, or have its own handle. If the distal capture component was not expandable, but instead a tapered shape like a dilator, the tissue will tear or expand when being crossed such that the subsequent capture of tissue may be less than ideal. An expandable distal capture mechanism 750, as shown in FIGS. 9A-D, will provide reduced tearing.

This distal capture component must also provide high capture forces when it is expanded, so tissue does not slip from the capture area, providing accurate shunt size and shape. Furthermore, for safety reasons the expandable distal capture mechanism failure mode ideally defaults to open. This means the device is ideally naturally self-expanding after it exits a flexible retention tube. Finally, the capture mechanisms preferably place most of the capture forces at the outer circumference of the captured area to minimize tissue slippage from the capture point. The devices shown in FIGS. 5, 6A and 6B are additional options. The device may ideally be preshaped such that when it comes out of the restraining device it expands, or it may expand to its full shape when the two ends of the device are pulled together or otherwise actuated. An expandable distal capture mechanism may also be made from an expanded nitinol wire or tube form and held about the catheter axis using radial arms, balloons or similar. Alternatively, high pressure shaped polymer balloons may also be used on their own or in combination with metal expandable structures to make an expandable distal capture component.

Once on the distal side of septum 730, the distal capture component may be expanded as shown in FIG. 9B, and brought into contact with the tissue 730. This may be accomplished a variety of ways, but ideally the expansion is actuated by actuating an actuator component on the handle of the catheter. The actuator may be a knob, lever, trigger, etc. . . . which releases a pre-shaped expandable distal capture component to expand, or forces the expansion of an expandable component into a useable shape. Ideally the expandable distal capture 750 component is rigid, so when it is brought together with the proximal capture component, a high capture force can be placed on the tissue so the tissue does not easily pull out from movements to the catheter, causing imperfect shunt size and shapes. The high capture force is preferably placed at the outer circumference, between the distal and proximal capture components, tightly pinching the tissue between the capture components at the captured area perimeter. The distal capture component preferably also holds high loading forces perpendicular to the capture, so when there is an in plane side load between the capture mechanism and the tissue the captured tissue does not pull out of the capture mechanism. The expandable distal capture mechanism may have a tissue trap or a very fine layer of mesh, braid, or solid material which traps all small tissue particulate to keep it from floating into the blood stream during the procedure, but preferably otherwise allows blood to pass through.

To optimize the shunt shape and size it is important to minimize the movement of the tissue capture point after device alignment, during capture and during cutting. This can be done by fixating the catheter at any point from proximal to distal. This is especially important after the catheter alignment just prior to capture. However, movement of the catheter after capture can still cause improper shunt shape and size if the loading force on the fossa ovalis tissue is sufficient to pull tissue from the capture point. Fixation of the catheter should control torque, advancement and withdrawal of the catheter relative to the catheter distal tip. The most efficient and safe way of performing this catheter fixation is to as solidly as possible attach the catheter outside the puncture site to the patient, as shown in FIG. 7. Because good fixation at the fossa ovalis is ideal for achieving an ideal aperture, good fixation outside the body is also ideal. One way to do this is to adhesively attach a catheter hub to the patient as close to the puncture site as possible. This catheter hub 600 can securely grasp the catheter shaft 610 or the catheter handle 620. If the patient moves the catheter hub 600 and catheter 610 will move with the patient, but the relative movement of the catheter distal tip with respect to the fossa ovalis will remain fixed. Alternatively, since the patient is sedated and generally does not move during the procedure, the proximal catheter shaft 610 or handle 620 can be fixed by a catheter hub 600 to the bedrail 630 or similar, as shown in FIG. 8 to keep it from moving. To facilitate the latter the patient's leg can furthermore be fixated to the bedrail to keep movements minimized.

After the catheter if fixated any remaining in-plane bias is preferably removed. This in-plane bias is a result of the catheter at the fossa ovalis crossing point being biased in-plane such that it slightly elongates the hole in the tissue which it is crossing through, as evidenced by high velocity blood jetting on doppler (TEE, TTE, ICE). The catheter shaft is preferably aligned in the fossa ovalis plane such that jetting as seen on doppler is minimized. This is done by torquing the catheter shaft, and if not preshaped, also actuating pull wires to deflect the distal tip. By minimizing blood jetting alongside of the catheter the shaft is brought into its original crossing point and in plane catheter shaft bias is removed. This will allow for a more accurate shunt shape and size.

Before the expanded distal capture mechanism 750 is pulled proximal to capture tissue the catheter 10 must be aligned to trap the tissue in its natural orientation. First, the proximal capture component 740, as seen on fluoro or echo is advanced such that the most distal face of the proximal capture mechanism is touching the fossa ovalis in its natural plane. To improve visibility of the proximal capture component radiopaque and/or echolucent filler is added. This will allow an in plane capture and support the accurate shunt shape and size. Next, the distal capture component, in an expanded state, is moved or actuated, is withdrawn such that its most proximal face is touching the fossa ovalis in its natural plane. Then the two devices are locked into place, with sufficient force between them to retain the tissue. Of course, the distal tissue capture mechanism may be advanced first.

Ideally the catheter has a component which, while fixated, can move the capture point slightly into the LA, in a controlled manner. This movement has two intended purposes. First, by moving the capture point slightly into the LA, the tissue is pulled slightly tight and over the blade, which helps facilitate an efficient cut. Secondly, if the tissue is tented slightly into the LA prior to cutting, as seen on Fluoroscopy or echocardiography, the clinician will know when the cut is complete by watching for the tissue to collapse from its tented position to its natural plane. This tenting of tissue is only expected to require a few millimeters of movement of the capture point. The amount of advancement is ideally indicated on the catheter or its handle. This advancement or tenting into the LA is expected to be less than 1 cm. The advancement mechanism can also be used for final fine adjustment of the linear capture point just before cutting the tissue.

For example, the distal capture component 750 may comprise an expandable balloon or a nitinol basket. The nitinol basket can be comprised of nitinol strands that, when released from confinement (in catheter 710, or the lumen of another element) expand into a circular capture element. The expanded nitinol basket may be flat, e.g., oriented largely parallel to the tissue 730, or it may be 3 dimensional, e.g., resembling a 3 dimensional diamond shape, such that when withdrawn it provides tissue tenting. In some embodiments the distal capture component 750 may pierce and hold the tissue. In some embodiments the tissue capture component 750 is larger than the cutting blade 716. In others, the capture component 750 is smaller than the cutting blade 716. In still others it is substantially the same size as the cutting blade 716, e.g., 6 mm.

In another embodiment the medical device assembly may include a proximal capture component 740 designed to remain at least partially on the proximal side of the septum 730. The proximal capture component may be attached to the guidewire 705, the sheath 700, or the catheter 710. It may also be attached to a proximal capture catheter 745. As such, proximal capture catheter 745 may ride over the guidewire 705, but inside a lumen of catheter 710. Proximal capture catheter 745 may be advanced by an actuator, or have its own handle.

In another embodiment, shown in FIGS. 9A-C, the assembly includes both proximal and distal tissue capture components, 740 and 750. In this embodiment the tissue capture components may be attached to the same or a different catheter or guidewire. In operation (FIG. 9B) the tissue capture components are brought together to hold the tissue between them, both retaining the tissue in place for the cutting blade 716, and also capturing the tissue for removal (FIG. 9C).

Figure 9D:
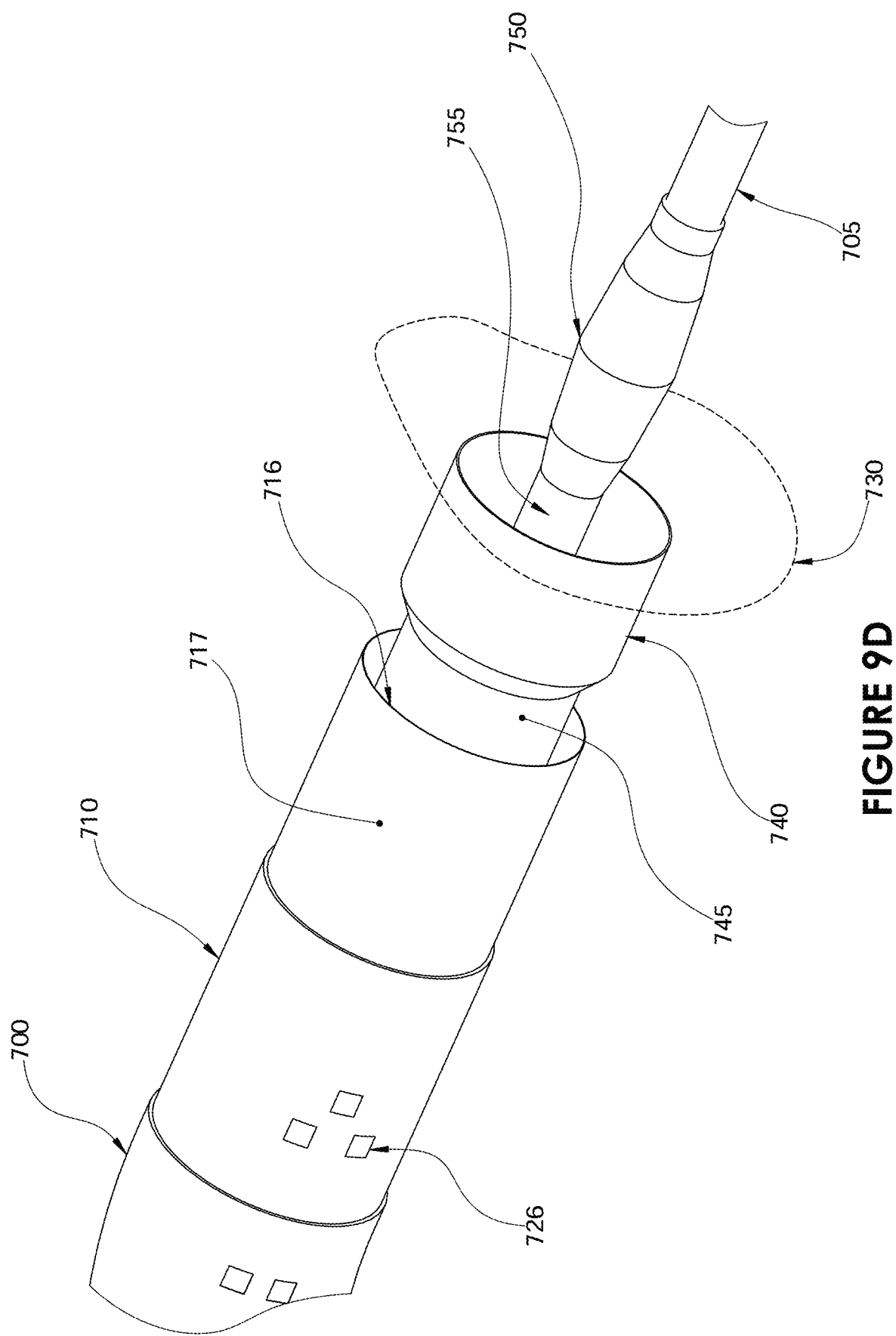
FIG. 9D is a partial perspective view of a catheter constructed according to the present disclosure.

FIG. 9D illustrates an exemplary device made of a distal capture component 750 on the end of a distal capture component shaft 755. The distal capture component 750 and distal capture component shaft 755 have a lumen to accommodate guidewire 705. The proximal capture component 740 is on a proximal capture component shaft 745, and both have a lumen large enough for the distal capture component shaft 755. The cutter 716 and the cutter shaft 717 both have lumens for the proximal capture component shaft 745. All three catheter shafts are assembled as shown and preferably can be advanced together or independently with respect to the other. In use the distal capture component 750 is advanced over a guidewire 705 already across the septum and placed so the proximal edge of this distal capture component 750 is touching the Left Atrial (LA) side of the septal tissue to be removed. Next the proximal capture component 740 is advanced to the Right Atrial (RA) side of this same septal tissue, such that the tissue to be cut and removed is trapped or captured with substantial force between the distal capture component 750 and the proximal capture component 740. The captured tissue then will not stretch as the cutter is advanced. Next the cutter 716 is advanced by advancing the cutter shaft 717 until the tissue captured between the distal capture component and proximal capture component is completely cut from surrounding tissue.

Once the capture is completed using the capture actuator on the handle it is important, for safety and performance reasons, to not easily allow the capture to be released. For this reason a locking mechanism is placed in the handle or in another part of the catheter so once the tissue capture is performed it is difficult to release the tissue without taking multiple steps. This will minimize any potential loss of cut tissue. To maximize accuracy of the shunt shape and size, as well as optimize safety, it is important to not allow any tissue to slip out of the capture system. To accomplish this it is ideal to place all capture forces at the outer circumference of the capture mechanisms. This may be accomplished by having an outer raised knife like edge on the outer most perimeter of the distal portion of the proximal capture mechanism and something similar on the proximal side of the distal capture mechanism. The diameter of these raised edge parts of the capture mechanisms should be just slightly less than the cutter blade. Also, to further improve capture teeth may be located on the raised edge. To maximize capture forces, without going beyond the strength of the catheter component, it is ideal to make the capture system spring loaded so a set range of capture forces will be obtained no matter the tissue thickness.

Alternatively, the cutter blade 716 and cutter blade shaft 717 can be advanced over the guidewire and dilator into the RA prior to advancement of the capture components. In some embodiments it will be advantageous to control tissue capture forces for safety and effectiveness. In these cases a sensor 770, and or a strain or force sensor 780 can be attached to the capture components. In a preferred embodiment the force sensor 780 is able to determine how much force is applied to the respective shafts, e.g., force sensor 780 determines how much force is applied to the proximal capture component shaft 745, while force sensor 781 determines how much force is applied to distal capture component shaft 755. By measuring these respective forces the operator is able to determine how firmly the tissue 730 is held between the components. Likewise, in embodiments with only one tissue capture component, the force sensor can identify how firmly that capture component holds the tissue. In the event that the tissue is not firmly held, the operator will be able adjust the positioning, remove the device and reapply it, or the like. Above all, the sensors on the capture component shaft can give the operator an indication of the safety of the operation. If the tissue is not affirmatively held, there is a risk it can break free creating a risk of stroke due to embolization. Accordingly, knowing how well tissue 730 is held by the tissue retention device(s) is critical. In other embodiments an actuator can apply a set amount of force between the capture components and can lock them in place.

In addition to or in the alternative to force sensors (780, 781) the device may comprise a sensor 770 on the proximal capture component shaft 745, and sensor 771 on the capture component shaft 755. Of course, sensors 770, 771 may be located on the capture components themselves as well. Sensors 770,771 may be used for one or more purposes, including determining the location of the shafts or components, visualizing the tissue, visualizing the procedure, sensing the impedance of the tissue, sensing the proximity of another sensor or component, and the like. Examples of such sensors include magnets, electromagnetic coils, electrodes, optical strain sensors, electrical strain sensors, cameras, fiber optics, ultrasound, pressure sensors and similar sensors. Likewise, markers such as radiopaque markers or ultrasound markers may be employed on the shafts or components.

There are three broad mechanisms for bringing the tissue capture components 740, 750 together. First, the distal mechanism 750 may be actuated to move proximally into the proximal mechanism 740. Doing so may tent the tissue or bring it into a lumen on the catheter 710 or the proximal mechanism. The tissue may also—preferably—be retained in a flat configuration (as shown). Second, the proximal mechanism 740 may be actuated to move into the distal mechanism 750. Doing so may tent the tissue or bring it into a lumen on the catheter 710 or on the distal mechanism. Finally, the two tissue capture mechanisms 740, 750 may be moved together, e.g., by a double bushing or double basket, to meet at the septum 730, which in some cases may remain in place. Depending on the shape of the mechanism, the tissue may remain flat (FIG. 9*b*) or may be tented (not shown).

In another embodiment, the components can be spring loaded in a way that consistently applies the same amount of force. For example, the movement of the tissue capture components 740, 750 and the cutting blade 716 may be controlled from one or more handle mechanisms. With reference to the '547 application the handle may have multiple portions that are linearly connected and axially movable along a central handle spindle. Relative movement of the portions controls the movement of the catheter components, and makes all motions uniform and controlled. Because the handle or the catheter hub controls how far the various components move, there is a greatly reduced risk of perforations in the left atrium, the procedure is faster, and less stressful for the operator. The handle may further include buttons or actuators that automate the movement of the handle portions.

In another embodiment, once the two capture mechanisms are in place, they are preferably held in place by a closure means. For example, the two capture mechanisms may have respective magnets that are strong enough to hold the capture mechanisms together absent operator input. Likewise, electromagnetic force could be utilized. Alternatively, a locking mechanism may be employed, either at the capture mechanisms (such as a friction lock, or a twist lock) or at the proximal end of the catheter, such as on a handle or actuator.

Figure 12A:
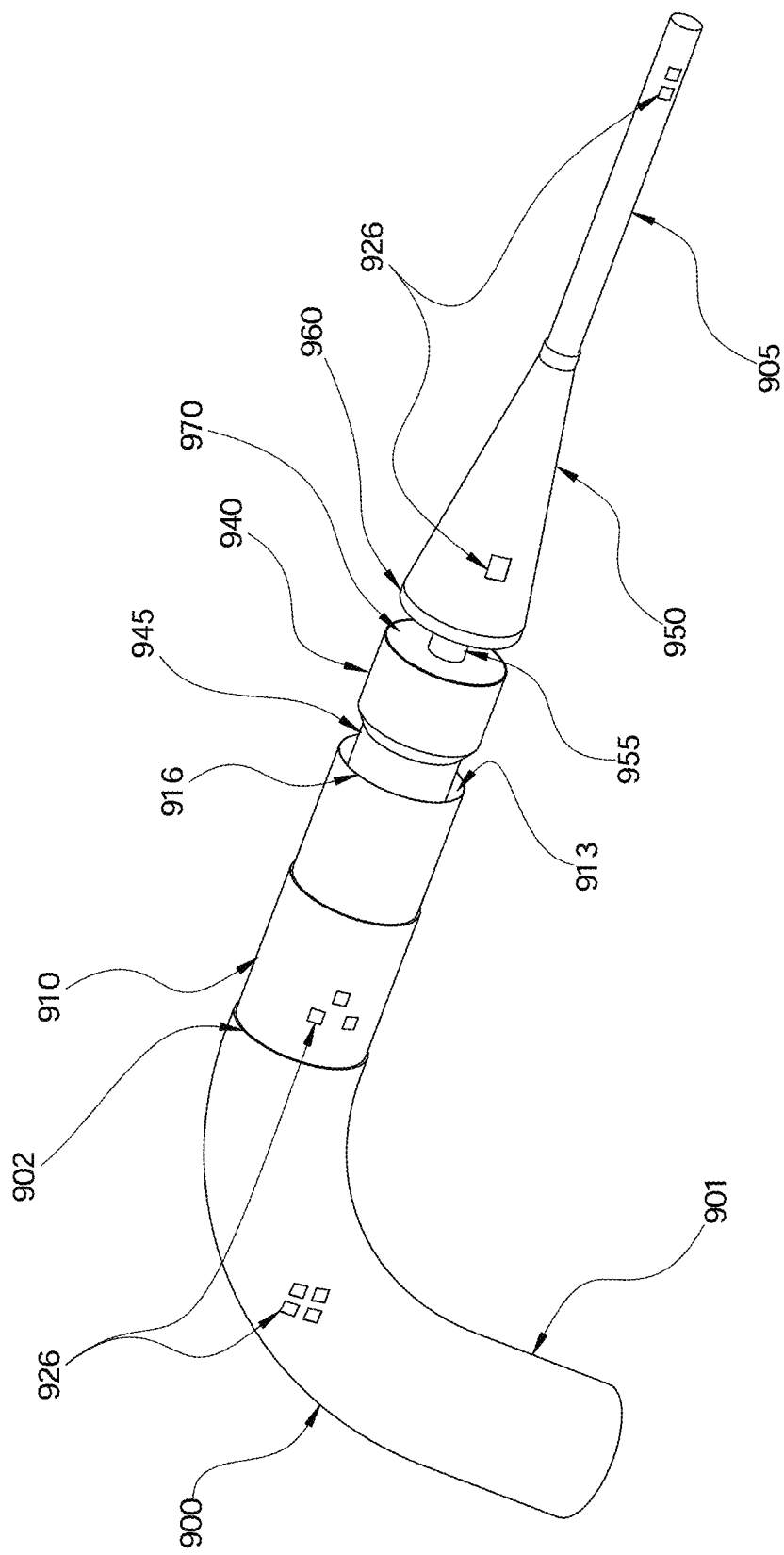
FIG. 12A is a partial perspective view of a catheter constructed according to the present disclosure.

Because the distal capture component 750 must cross the septum it is likely to inflict some damage on the tissue. There can be a tradeoff between inflicting minimal damage to the tissue, but yet supporting the cutting action and providing sufficient capture force so the tissue is safely removed. To minimize damage to the tissue the distal capture component may be made of a tapered cone as shown in FIG. 12A, a double tapered cone as shown in FIG. 12*b*, an expandable metal frame like the nitinol design shown in FIG. 12*c*, or an expandable balloon design as shown in FIG. 12*d*. The distal capture component 950 may be designed so that it has a tight fit with the cutter 916, or act as a back-stop for the cutter 916, both facilitating the cutting action. The distal capture component 950 may also be designed to hold a cutter 951 on its proximal end, as seen in FIG. 12e, such that a proximal and distal cutter act in concert to cut the tissue. The device design may also contain a cutter mounted only to the distal capture component. The distal capture component 950 may also be designed with an auger or cork screw 952 (FIG. 12O type configuration to reduce septum tissue tearing while crossing.

The proximal capture component 940 is designed to fit with the distal capture component 950 so that it provides a high capture force of the tissue, especially at its outer circumference. Interface features of both of these components may be designed with high capture force, roughening surfaces or barbs (12h), edges to the surfaces (12g), and vacuum ports (12i) as seen in FIGS. 12h-i. As detailed above, the capture components may also comprise a balloon, a pigtail (not shown), an expandable nitinol basket (not shown), an disk or expandable disk (not shown) or similar means. In some embodiments a single capture mechanism can hold both proximal and distal sides of the tissue. A balloon for example may be narrow in the middle and broad at both ends, essentially surrounding the tissue it passes through. An Auger can have surfaces on both sides of the tissue as well, for example.

In another embodiment the guidewire may include a tissue capture component, such as a pigtail or hook. The tissue cut from the interatrial septum to complete the aperture is positively retained by the guidewire and pulled inside the catheter 710 when the guidewire is withdrawn from the body and into catheter 710. While the guidewire has been described as having either a balloon or pigtail, other articulation and tissue retention devices are contemplated. In particular a disc device can be utilized. The disc device may include one disc that is navigated to the distal side of tissue 730, or may include a disc on each side of the tissue 730. The two discs may be actuated to secure the tissue between them. The disc may be expandable having a small diameter when crossing the septum and a larger diameter when securing the tissue. Cutter 716 may ride over the discs, pulling them into lumen 713, to cut the tissue which then remains retained between the two discs and is removed from the body.

Figure 11:
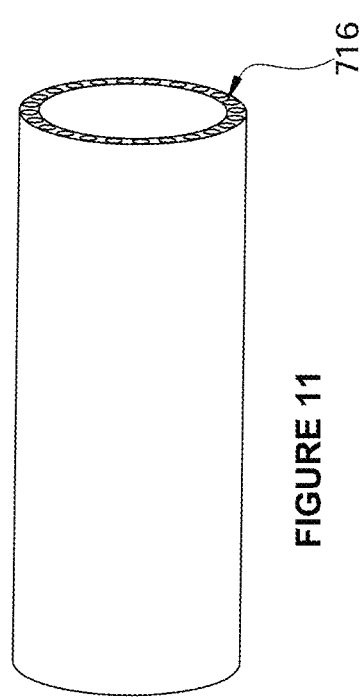
FIG. 11 is a partial perspective view of a cutter constructed according to the present disclosure.

In one embodiment the assembly may not cross the tissue 730. As shown in FIG. 11, this assembly omits the guidewire 705 and could optionally omit the sheath 700, though in embodiments the sheath 700 still provides stability and anchoring as discussed above.

In this embodiment the distal end of catheter 710 is delivered or directed to the tissue 730 as discussed above. A proximal tissue retention means 740 may be employed to grab the tissue from the proximal side. For example, a corkscrew device 740 may be engaged with the tissue such that it holds the tissue in place. Other mechanisms are contemplated, including a cylinder (as pictured in FIG. 9D), hooks, forceps, barbs, adhesives, and suction. For example, catheter 710 may employ one or more suction ports 735 to apply suction to the tissue 730. Suction ports 735 may be arranged on opposite sides (e.g., every 180 degrees), every 90 degrees, in a ring of ports, or in a continuous circle inside of or outside of the cutting mechanism 716. In this embodiment the suction is employed to remove any tissue or debris that comes loose during the procedure, ensuring that no embolic material escapes.

In some embodiments ultrasound or similar can be applied to the blade to reduce the force to cut tissue. This may be especially advantageous for cutting through fibrous tissue. Also, an ultrasonic pressure reduction, or vacuum assistance, within the lumen of the cutter can be used to help pull tissue into the blade.

Figure 10C:
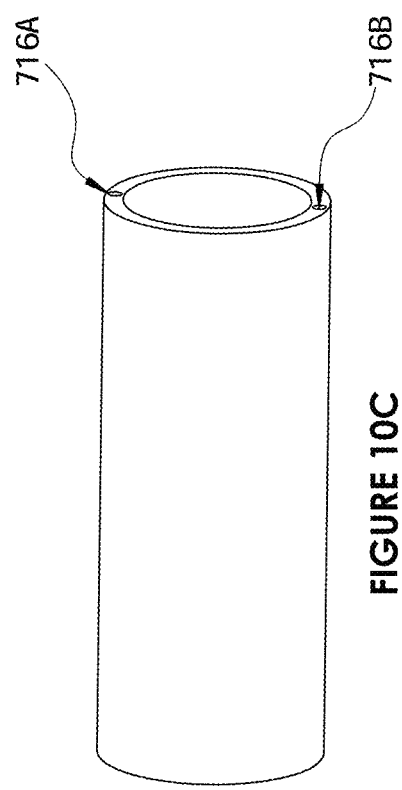
FIG. 10C is a partial perspective view of a cutter constructed according to the present disclosure.

As discussed in the '547 application, an energy source cutter may also reduce cutting forces. These include a laser or RF cutter with multiple emitters 716 a, b (as shown in FIG. 10C) or rotating (as shown in FIG. 10D) designs.

Figure 13A:
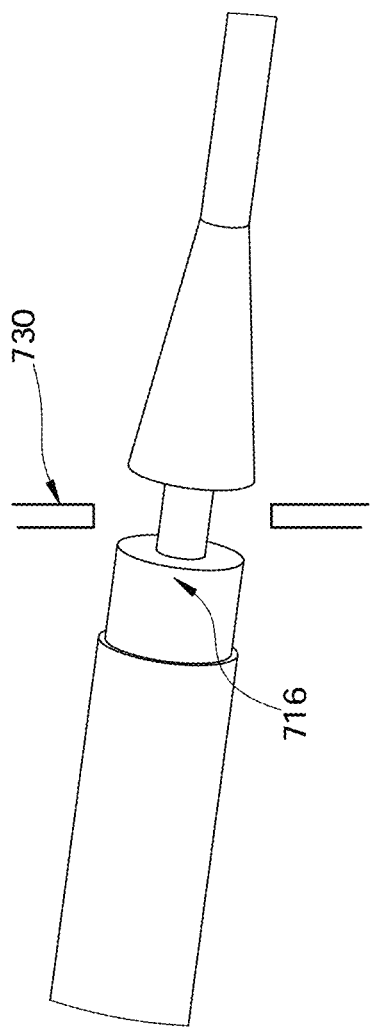
FIG. 13A is a partial perspective view of the distal end of a catheter constructed according to the present disclosure making a second cut.
Figure 13B:
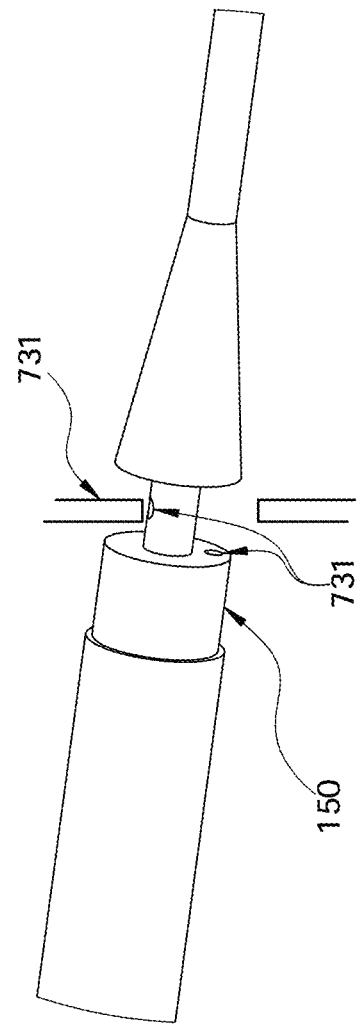
FIG. 13B is a partial perspective view of the distal end of a catheter constructed according to the present disclosure making a second cut.

Once a hole is created in the septal wall there are two ways to increase the area of removed tissue. The first is to simply create another hole. This may be done by using a one cutter device multiple time to cut multiple holes, or a device which creates multiple holes each time it is used. In any case, it is the total effective cross-sectional surface area of the shunt which is important clinically. If many smaller holes are used their measured total cross-sectional will likely need to be slightly larger than the cross section of a single large shunt to get a similar total effective cross-sectional area, due to the boundary layer effect. The second way to increase the area of removed tissue in the wall is to enlarge a present hole. To enlarge an existing hole the cutter 716, which may be a blade, energy source or the like as described above, is preferably aligned in the plane of the septum 730 as in FIG. 13a. Then the cutter 716 must be moved within the plane of the septum 730 to engage the septal tissue edge, 731 as shown in FIG. 13b. A tissue cookie can be cut and removed, or the laser or RF vaporizing technologies can be used to vaporize all the additional tissue meant for removal. The movements, cutter, and tissue to be cut will be relatively small compared to common imaging capabilities, and the imaging capability may only be 2D. Accordingly, the catheter 710 includes sensors 780 such an impedance, ultra sound, OCR, etc. to localize the tissue to be cut with respect to the cutter. The sensor 780 could alternatively be a suction port or orifice (a hole). The sensor(s) can be on the device, in the cutter element, or anywhere in the cutting region. In one embodiment the same optical fiber used for laser cutting can also be used for tissue sensing, or the same RF electrodes used for tissue cutting can be used to sense the orientation of tissue within the cutter region.

In the suction case if a low pressure can be pulled on the orifice it may be expected that it is blocked by tissue and tissue is ready to cut. Likewise, a biopsy type forceps with sensing capability is used to increase hole diameter by grabbing a portion of tissue for the cutter to cut. To facilitate controlled catheter movements a catheter handle can be locked in place with respect to the septal wall, e.g., by fastening the handle, the sheath, or the catheter to the patient's bedside.

Regardless of the tissue removal or retention means, it is especially advantageous to include a tissue collection device when attempting a second cut. For example, the catheter may include a lumen or compartment at the distal end to retain the tissue. Likewise, under suction the device may include a tissue trap, such that fluid, blood, or other material may pass, but tissue is retained in the trap. The physician then may monitor the trap to determine that the tissue removed from the septum has been captured, and is not still in the heart. Such a monitoring may be automatically provided, or may be manual by the physician. It is advantageous if such monitoring can be conducted before the catheter is removed from the patient, and as such in one embodiment the trap is exterior to the body and readily accessible by the physician. In another embodiment, the trap is automatically monitored by a sensor, such as an electrode, visual examination, pressure sensor, or the like for the presence and volume of tissue.

Typically the device types described herein work best if there is no bias, or force on the tissue in any direction other than what is necessary to capture and cut. The exception is a device used to increase an existing hole's size, in which case biasing the shaft and cutter into the side of the previous hole is necessary. In general though, if there is bias in or out of the septal plane during capture for instance, the tissue will likely be stretched over the capture components prior to capture, making the resulting hole smaller than expected. Likewise, if the bias is within the septal plane prior to capture, the device shaft will elongate or tear the hole such that the capture has minimal tissue on one side and bunched tissue on the other. If a cut is made in the latter situation, the cutter may pass through, on one side, the hole created by the bias, leaving an elongated hole. Also, if part of the cut passes through a hole stretched by bias, the tissue around the shaft will not be complete, creating an increased safety risk that would need mitigating.

Figure 14:
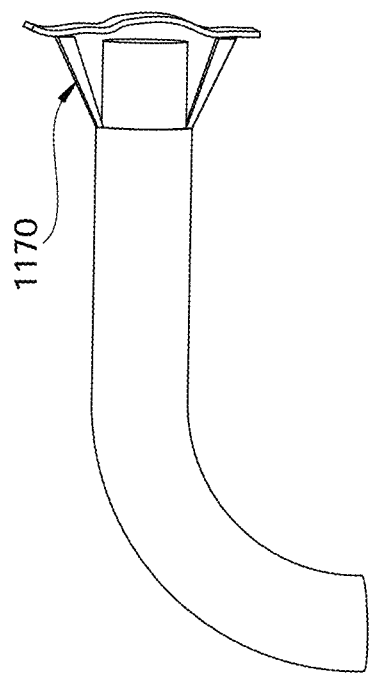
FIG. 14 is a partial perspective view of the distal end of a catheter constructed according to the present disclosure.

To remove bias—device stability, control and feedback is needed. Stability can be achieved at least three ways. First, a distal structure 1170 as in FIG. 14, attached to the outer sheath can engage the septal tissue, allowing all adjustments to be with respect to it. This frame structure may be at least partly disconnected from the proximal components to minimize unintended forces. The frame structure may consist of one or more struts extending from the catheter or sheath, designed to lean against the tissue and hold the catheter and cutter orthogonally to the tissue. Likewise, in another embodiment the structure may be a hood. A hood structure would also allow a suction to remove all blood and provide direct visualization of the septum. In another example the distal structure 1170 may be a balloon on the outer surface of the sheath, such that when inflated the balloon structure matches the contour of the septum and provides for an orthogonal guide to the sheath, catheter, or blade. In each case, the orthogonal guide is preferably collapsible for delivery into the atrium.

Second, the device, such as the sheath or catheter shaft, can be affixed securely to the patient's puncture site via a catheter holder, allowing all adjustments to be with respect to the puncture site and therefore the septum. Finally, the catheter handle can be affixed to the patient, drape, bed rail mount/platform, or similar via a catheter holder.

A catheter holder would secure either the catheter shaft, catheter handle, or both. The combination of the catheter handle and catheter holder would secure and hold constant the catheter shaft, and therefore hold constant the distal end of the catheter tip, from rotation, bending, longitudinal movements, alignment, bias, tissue capture actuation and cutter operation. The operator could then control fine adjustable movements of the handle or catheter holder in order to make fine prescribed movements to the catheter distal tip, for more accurately and safely cutting a hole in the interatrial septum.

Since each of these progressively is further from the septum, they progressively become less stable. However, each is more stable than the clinician simply controlling localization with his hand. Control of the distal tip of the devices is achieved through the device rotation, shaft deflection, bending of the shaft, and actuation of the distal components. In some cases, for precise aperture creation, these critical control movements may be less than 1 mm, making the previously mentioned device stability critical. As input into the decision to manipulate the controls for proper aperture creation precise feedback is necessary. Feedback described above included, bias force sensing, tissue thickness sensing, device localization sensing, visual handle controls of distal catheter elements, as examples. Most of the control and feedback are in reference to some stable device reference point established somewhere along the catheter, as necessary to deliver a precise aperture quickly and safely.

In another embodiment, the cutting means is allowed to "float" with respect to the catheter, such that it is contact with the tissue that governs the orientation of the cutting means, rather than the orientation of the catheter. In particular, if the bottom side of a circular cutter contacts the tissue first, the cutter will pivot as it is pushed forward, for example, so that only the top portion moves forward until the entire cutter is substantially in contact with the tissue. For example, in one embodiment the cutter may be attached to the medical device via a central shaft, and spaced from the catheter via springs around the periphery, such that under light pressure from the fossa, the cutter compresses one or more springs, but does not initially compress the others, causing the cutter face to move into an orthogonal position vis a vis the tissue. As the cutter comes fully into contact with the tissue, the pressure from the catheter continues to rise and it is pushed orthogonally through the tissue.

The invention claimed is:

1. A medical device assembly comprising:
    a catheter assembly, the catheter assembly comprising:
        a catheter shaft, the catheter shaft having a central lumen and a radiopaque marker,
        a sharp shaped blade, the sharp shaped blade comprising:
            a blade cutting edge that is oriented at a substantially right angle to a longitudinal axis of the catheter shaft,
        a proximal tissue retention device,
        a distal tissue retention device,
    an actuator, the actuator configured to reduce a gap between the proximal and distal tissue retention devices; wherein the proximal tissue retention device and the distal tissue retention device are configured to retain a cut tissue between them when the gap is reduced; and
    a first steering element configured to orient the shaped blade toward a tissue.

2. The medical device of claim 1, further comprising a locking mechanism configured to hold a force on the tissue between the proximal and distal tissue retention devices.

3. The medical device of claim 1, wherein the first steering element comprises a pull wire.

4. The medical device of claim 1, wherein the first steering element comprises a shape memory material or a preformed bend.

5. The medical device of claim 1, further comprising:
    a sheath, the sheath comprising:
        a lumen, the lumen configured to contain the catheter inside the sheath,
        an elongated sheath shaft, the sheath shaft having a first bend region, a central lumen and a distal end, and
        wherein the first steering element is on the sheath, and is configured to move the first bend region from a substantially linear orientation to a second orientation substantially perpendicular to a longitudinal axis of the sheath.

6. The medical device of claim 1, wherein the actuator forces the proximal and distal tissue retention devices together with a preset force.

7. The medical device of claim 6, wherein the proximal tissue retention device and the distal tissue retention device apply the preset force at a respective outer edge of each of the proximal and distal tissue retention devices.

8. The medical device of claim 1, wherein the distal tissue retention device is expandable.

9. The medical device of claim 8, further comprising a second actuator, wherein the second actuator is configured to expand the distal tissue retention device.

10. The medical device of claim 8, wherein the distal tissue retention device expands to an open position when it exits one of a catheter, a tube, or a sheath.

11. The medical device of claim 1, wherein an outer diameter of the proximal tissue retention device is substantially the same as an inner diameter of the sharp shaped blade.

12. The medical device of claim 11, wherein the blade has its sharp edge on its inner diameter.

13. The medical device of claim 1, where in the distal tissue retention device further comprises a tissue trap.

14. The medical device of claim 1, further comprising a catheter hub, the catheter hub configured to secure the catheter system to a stable object.

15. The medical device of claim 1 further comprising a means for rotating the sharp shaped blade.

16. The medical device of claim 1, wherein the sharp shaped blade comprises an expandable basket with multiple cutting points.

17. A medical device assembly comprising:
a catheter assembly, the catheter assembly comprising:
   a catheter shaft, the catheter shaft having a central lumen,
   a shaped blade, the shaped blade comprising:
      a blade cutting edge that is oriented at a substantially right angle to the longitudinal axis of the catheter,
   a proximal tissue retention device,
   a distal tissue retention device,
   an actuator, the actuator configured to force the proximal and distal tissue retention devices together with a preset force;
   a locking mechanism configured to lock the proximal and distal tissue retention devices in place; and
   a first steering element configured to re-orient the shaped blade from a first position substantially orthogonal to the longitudinal axis of the catheter shaft to a second position substantially parallel to the longitudinal axis of the catheter shaft.

18. A method of treating a heart comprising the steps of:
inserting a catheter into the right atrium of the heart, the catheter comprising:
   a shaft,
   a distal catheter lumen,
   a sharp shaped cutting blade arranged around the distal catheter lumen,
   a proximal tissue retention device, the proximal tissue retention device having a first position and a second position,
   a distal tissue retention device, the distal tissue retention device having a first position and a second position,
an actuator connected to at least one of the tissue retention devices,
a steering mechanism,
while the catheter is in the right atrium, moving a portion of the catheter into the left atrium,
actuating the actuator to lock the tissue retention devices in place with a portion of the interatrial septum held between them,
cutting an aperture in the interatrial septum between the right atrium and the left atrium,
removing a cut tissue from the right atrium.

* * * * *